(12) United States Patent
Tsuruwaka et al.

(10) Patent No.: US 9,777,254 B2
(45) Date of Patent: Oct. 3, 2017

(54) **CELL LINE DERIVED FROM THREAD-SAIL FILEFISH (*STEPHANOLEPIS CIRRHIFER*)**

(71) Applicant: Independent Administrative Institution, Japan Agency for Marine-Earth Science and Technology, Yokosuka-shi, Kanagawa (JP)

(72) Inventors: Yusuke Tsuruwaka, Yokosuka (JP); Tomohisa Ogawa, Yokosuka (JP); Yuji Hatada, Yokosuka (JP)

(73) Assignee: INDEPENDENT ADMINISTRATIVE INSTITUTION, JAPAN AGENCY FOR MARINE-EARTH SCIENCE AND TECHNOLOGY, Yokosuka-shi (JP)

(*) Notice: Subject to any disclaimer, the term of this patent is extended or adjusted under 35 U.S.C. 154(b) by 107 days.

(21) Appl. No.: 14/418,781

(22) PCT Filed: Jul. 30, 2013

(86) PCT No.: PCT/JP2013/070627
§ 371 (c)(1),
(2) Date: Jan. 30, 2015

(87) PCT Pub. No.: WO2014/021329
PCT Pub. Date: Feb. 6, 2014

(65) Prior Publication Data
US 2015/0175958 A1 Jun. 25, 2015

(30) Foreign Application Priority Data
Jul. 31, 2012 (JP) .................................. 2012-169378

(51) Int. Cl.
*C12N 5/071* (2010.01)
*C12N 5/10* (2006.01)
*C12N 15/87* (2006.01)

(52) U.S. Cl.
CPC ........ *C12N 5/0602* (2013.01); *C12N 2510/00* (2013.01); *C12N 2510/04* (2013.01); *C12N 2517/02* (2013.01)

(58) Field of Classification Search
CPC .... C12N 5/0602; C12N 5/06; C12N 2506/00; C12N 15/87; C12N 2510/00
USPC ......................................... 435/325, 377, 455
See application file for complete search history.

(56) References Cited

U.S. PATENT DOCUMENTS

2004/0029102 A1  2/2004  Ono et al.

FOREIGN PATENT DOCUMENTS

JP    2008-220198 A    9/2008

OTHER PUBLICATIONS

Hye Suck An et al. (2011) Genes & Genomics, vol. 33(6), 605-611.*
Nakatani (2010) <Heisei 22 Nendo The Zoological Society of Japan OM-sho Poster Happyo Yoshi> "Shu no Kotonaru Gyoruikan de Harabire no Tayosei o Motarasu Mechanism no Kaimei", The Zoological Society of Japan Dai 81 Kai Taikai Yokoshu Program [online], 2010; The Zoological society of Japan Gakkai Jimukyoku, Tokyo-To Bunkyo-Ku.*
Egami "Fish Cell Culturing" Special Issue: Molecular Biology of Fish, Protein, Nucleic Acid and Enzyme, vol. 34 (3) (1989), 186-192, partial English Translation.*
Fan et al. (2010) Cytotechnology, vol. 62(3) 217-223.*
Ebitani et al. (1988) Zoological Science, vol. 5, 183-186.*
Cheng et al. (2010) J. Fish. Dis., vol. 33(2), 161-169.*
Christen et al. (2010) BMC Biology, vol. 8:5, pp. 1-14.*
Matsuura et al. (2014) Ichthyological Research, vol. 62(1), 75-113.*
de Lima et al. (2011) Comparative Cytogenetics, vol. 5(1), 61-69.*
Ebitani et al., "An Established Marine Fish Cell Line with High Plating Efficiency," Zoological Science, vol. 5, May 19, 1988, pp. 183-186.
Egami, "Fish Cell Culturing," Special Issue: Molecular Biology of Fish, Protein, Nucleic Acid and Enzyme, vol. 34, No. 3, Feb. 21, 1989, pp. 186-192, along with a partial English translation.
Fan et al., "Establishment of a Turbot Fin Cell Line and its Susceptibility to Turbot Reddish Body Iridovirus," Cytotechnology, vol. 62, No. 3, Jun. 2010 (published online May 26, 2010), pp. 217-223 (9 pages total).
Hasegawa et al., "A Cell Line (CFK) from Fin of Isogeneic Ginbuna Crusian Carp," Fish Pathology, vol. 32, No. 2, 1997, pp. 127-128.
Kikuchi et al., "Study of Culture Condition for Industrial Application of Scorpionfish Cell Line," Kanto Gakuin University, Research Presentation, 2009, pp. 170-171, along with an Partial English translation.
Meguro et al., "A Cell Line Derived from the Fin of Japanese Flounder, *Paralichthys olivaceus*," Gyobyo Kenkyu, vol. 26, No. 2, 1991, pp. 69-75.
Nakatani, "Determination of Mechanism of Pelvic Fin Variation between Fish Species," Abstracts of poster presentations winning the OM award of The Zoological Society of Japan, 2010, pp. 23-24, along with a partial English translation.

* cited by examiner

*Primary Examiner* — Anne Marie S Wehbe
(74) *Attorney, Agent, or Firm* — Birch, Stewart, Kolasch & Birch, LLP

(57) ABSTRACT

The first object of the present invention is to provide an immortalized cell line derived from a thread-sail filefish. The first object of the present invention can be solved by a cell line or a passage strain thereof derived from a living body part of a fish of the family Monacanthidae, wherein the cell line or the passage strain thereof is capable of being subcultured substantially without limitations. The second object of the present invention is to provide a pluripotent stem cell derived from a thread-sail filefish. The second object of the present invention can be solved by a cell line or a passage strain thereof derived from a living body part of a fish of the family Monacanthidae, wherein the cell line or the passage strain thereof is positive for at least a cell marker selected from a group consisting of TRA-1-60, OCT4 and SSEA-3.

19 Claims, 33 Drawing Sheets

CELL LINE DERIVED FROM THREAD-SAIL FILEFISH (*STEPHANOLEPIS CIRRHIFER*)

CROSS REFERENCE TO RELATED APPLICATION

This application is the National Phase of PCT/JP2013/070627 filed on Jul. 30, 2013, which claims priority under 35 U.S.C. 119(a) to Patent Application No. 2012-169378 filed in Japan on Jul. 31, 2012, the entire contents of which are hereby expressly incorporated by reference into the present application.

TECHNICAL FIELD

The present invention relates to a cell line or a passaged strain thereof derived from a living body part of a fish of the family Monacanthidae that appears morphologically like a fibroblast.

BACKGROUND ART

Fish cells derived from various fishes possess properties that resemble those of animal cells derived from mammals. Besides, fish cells can generally be cultured at relatively low temperatures in abroad growable temperature range. Therefore, cultured fish cells seem to be highly promising in industrial and research applications from the viewpoint of production of substances derived from living bodies because cultured fish cells can be substituted for animal cells.

Established cell lines derived from corneal epithelial cells of sturgeons and those derived from scorpion fish caudal fins are known in the field of cultured fish cells (see, for example, Patent Documents 1 and 2, the entire contents of which are incorporated herein by reference for the purpose of supporting the disclosure of the present invention). Such established cell lines are expected not only to provide cells that can be substituted for animal cells but also to take a significant role in clarification of the ecology of sturgeon and that of scorpion fish and in raising these fishes.

Fishes of the family Monacanthidae in the order Tetradontifomes including thread-sail filefish (*Stephanolepis cirrhifer*) are coated with tough skin over the entire body and, when cooking such a fish, the skin can entirely be peeled off at a time. Among the family Monacanthidae, thread-sail filefish (*Stephanolepis cirrhifer*) is cherished by many people both as fish foodstuff to be taken as raw fish and as fish foodstuff to be cooked for tasty dishes.

PRIOR ART DOCUMENTS

Patent Documents

Patent Document 1: JP No. 2004-024192 A
Patent Document 2: JP No. 2008-220198 A

DISCLOSURE OF THE INVENTION

Problems to be Solved by the Invention

While thread-sail filefish (*Stephanolepis cirrhifer*) is being cherished by many people as fish foodstuff, thread-sail filefishes that are currently being marketed are natural ones and the fishery yield of thread-sail filefish varies with season. On the other hand, there is not any established farming technology for thread-sail filefish at present, although various attempts have been made to develop thread-sail filefish farming techniques to date.

Deaths of farmed fishes due to infectious diseases caused by bacteria and viruses and those due to chemicals and heavy metals that are toxic to fish cells have been a serious problem for fish farming. Thus, fish cell lines can take an important role in diagnoses of infectious diseases caused by viruses, in manufacturing vaccines that are effective against virus infections and in testing cell toxicity for the purpose of solving the problem of deaths of farmed fishes. The inventors of the present invention thought that a clue to solving the problem of deaths of farmed thread-sail filefishes can be obtained and a remarkable development of thread-sail filefish farming can be achieved when immortalized cell lines of thread-sail filefish are available. Particularly, fish cell lines can generally be cultured at low temperatures but show a small growth rate if compared with mammalian cell lines. Therefore, if immortalized cell lines of thread-sail filefish can be cultured at low temperatures and show a growth rate comparable to the growth rates of mammalian cell lines, the immortalized cell lines of thread-sail filefish can be cultured easily and rapidly, thereby being expected to contribute to a rapid progress in the field of development of thread-sail filefish farming techniques.

Meanwhile, if pluripotent stem cells of not only thread-sail filefish but also of various fishes in general are available, it will be possible to obtain tissue cells, which were hitherto difficult to be collected, by inducting differentiation of the cells into specific cells. Then, by turn, it will be possible to look into the causes of fish diseases and the onset mechanisms of such diseases. Additionally, it will then be possible to evaluate the effect of a medicinal agent relative to a specific disease and the toxicity thereof by using the cells that developed the onset of the disease after the differentiation induction. Thus, pluripotent stem cells of fishes can be expected to contribute to the development of fish farming techniques in the future.

As pointed out above, the research and development of thread-sail filefish farming techniques can remarkably be promoted by using immortalized cell lines and pluripotent stem cells of thread-sail filefish. However, neither a cell line nor a pluripotent stem cell of thread-sail filefish that has been established is known to date.

In view of the above-identified facts, it is therefore the first object of the present invention to provide an immortalized cell line derived from a thread-sail filefish. The second object of the present invention is to provide a pluripotent stem cell derived from a thread-sail filefish. The third object of the present invention to provide a method of manufacturing and a method of utilizing a cell line derived from a thread-sail filefish.

Means for Solving the Problems

The inventors of the present invention firstly paid attention to the fact that fish cells can be cultured at low temperatures and studied to establish fish cell lines. Then, the inventors of the present invention tried to grow various tissue cells, using fins of various fishes including sea bream, horse mackerel and shark. However, most of cells obtained in such a manner are those not to be even subcultured, let alone those with a high growth rate. Thus, the inventors of the present invention made intensive research efforts and eventually succeeded in manufacturing an immortalized cell line that is capable of being subcultured and derived from the dorsal fin of a thread-sail filefish as a result of appropriately selecting different fish species and using different subculturing techniques. Moreover, surprisingly, the obtained cell line could be cultured at a growth rate substantially same as or higher than the growth rate of mammalian cell lines even when it was cultured at temperatures of 25° C. which is not significantly different from the room temperature. More surprisingly, the cell line derived from a thread-sail filefish that the inventors of the present invention obtained expressed a part of the cell markers that evinced pluripotent differentiation and could be metamorphosed into various morphologically different cells by changing the culturing conditions. The present invention has been completed on the basis of these successful researches and findings.

Thus, according to the present invention, there is provided a cell line or a passage strain thereof derived from a living body part of a fish of the family Monacanthidae, wherein the cell line or the passage strain thereof has property (1) shown below:
(1) a property of being capable of being subcultured substantially without limitations.

Preferably, a cell line or a passage strain thereof according to the present invention as defined above further has property (2) shown below:
(2) a property of being similar to fibroblast in morphology.

Preferably, a cell line or a passage strain thereof according to the present invention as defined above further has property (3) shown below:
(3) a property of being able to be cultured to form a multilayer structure.

Preferably, a cell line or a passage strain thereof according to the present invention as defined above further has property (4) shown below:
(4) a property of having a number of chromosomes that is in accordance with the frequency distribution having a maximum value of 66, a minimum value of 32 and a mode of 33.

Preferably, in the property (4) as described above, the frequency of 33 chromosomes of the mode takes about 90% of all the frequencies in the frequency distribution.

Preferably, a cell line or a passage strain thereof according to the present invention as defined above further has property (5) shown below:
(5) a property of showing a doubling time of about 14 to 28 hours when the cell line or the passage strain thereof is cultured in a culture vessel having a bottom area of 75 cm$^2$, using a Leibovitz's L-15 culture medium containing FBS by 10%, at 25° C. in the absence of $CO_2$ with an initial cell number of about $1.0 \times 10^6$ cells/ml.

In another aspect of the present invention, there is provided a cell line or a passage strain thereof derived from a living body part of a fish of the family Monacanthidae wherein the cell line or the passage strain thereof is positive for at least a cell marker selected from a group consisting of TRA-1-60, OCT4 and SSEA-3.

Preferably, a cell line or a passage strain thereof according to the present invention as defined above is similar to fibroblast in morphology.

Preferably, the cell line or the passage strain thereof according to the present invention as defined above has an ability of differentiating into at least a type of cells selected from a group consisting of muscle cells, muscle cell-like cells, epithelial cells, epithelial cell-like cells, nerve cells, nerve cell-like cells, adipocytes, adipocyte-like cells, immune cells, immune cell-like cells, hepatocytes and hepatocyte-like cells.

For the purpose of the present invention, the fish of the family Monacanthidae is a fish selected from a group consisting of the genus *Stephanolepis*, the genus *Thamnaconus*, the genus *Cantherhines*, the genus *Aluterus* and the genus *Rudarius*.

For the purpose of the present invention, the fish of the family Monacanthidae is a thread-sail filefish (*Stephanolepis cirrhifer*).

For the purpose of the present invention, the living body part is a fin located at the back, at the chest, at the abdomen, at the buttock or at the tail.

In still another aspect of the present invention, there is provided a cell line or a passage strain thereof derived from the dorsal fin of a thread-sail filefish (*Stephanolepis cirrhifer*) with the accession number of NITE BP-1369.

In still another aspect of the present invention, there is provided a method of manufacturing a cell line or a passage strain thereof according to the present invention as defined above, which comprises a step of subjecting a cell isolated from a living body part of a fish of the family Monacanthidae to subcultures for not less than 70 times.

In still another aspect of the present invention, there is provided a transformant obtained by transfecting a foreign gene into a cell line or a passage strain thereof according to the present invention as defined above.

In still another aspect of the present invention, there is provide a method of manufacturing a transformant comprising a step of transfecting a foreign gene into a cell line or a passage strain thereof according to the present invention as defined above to obtain a transformant.

In still another aspect of the present invention, there is provide a method of manufacturing an expression product of a foreign gene comprising a step of obtaining an expression product of a foreign gene from a transformant obtained by transfecting the foreign gene into a cell line or a passage strain thereof according to the present invention as defined above.

In still another aspect of the present invention, there is provided a kit for manufacturing a transformant, the kit comprising a cell line or a passage strain thereof according to the present invention as defined above, a vector and an instrument for transfection.

In still another aspect of the present invention, there is provided a kit for manufacturing a differentiated cell, the kit comprising a cell line or a passage strain thereof according to the present invention as defined above, a culture medium and a culture vessel.

Preferably, a kit according to the present invention as defined above further comprises serum.

Preferably, the serum as defined above is a type of serum selected from a group consisting of mammalian serum, fish serum and a serum replacement.

Preferably, the culture medium is at least a type of culture medium selected from a group consisting of culture media for mammalian cells, culture media for insect cells and culture media for fish cells.

Preferably, the culture vessel is at least a type of culture vessel selected from a group consisting of culture vessels coated at the bottom surface with cell adhesion molecules and culture vessels not coated at the bottom surface with any cell adhesion molecules.

In still another aspect of the present invention, there is provided a method of manufacturing a differentiated cell, the method comprising a step of culturing a cell line or a passage strain thereof according to the present invention as defined above in a culture vessel coated at the bottom surface with cell adhesion molecules or not coated at the bottom surface with any cell adhesion molecules, using a culture medium for mammalian cells, insect cells or fish cells, the culture medium not containing any serum or containing mammalian serum, fish serum or a serum replacement.

In still another aspect of the present invention, there is provided a cultured cell sheet comprised of a cell line or a passage strain thereof according to the present invention as defined above.

In a further aspect of the present invention, there is provided a method of manufacturing a huge cocoon-like colony, the method comprising a step of manufacturing a huge cocoon-like colony comprised of cells that are identified by staining with active alkaline phosphatase and found to be positive for NANOG, OCT4, TRA-1-60 and SSEA-3 from a cell line or a passage strain thereof according to the present invention as defined above.

Advantages of the Invention

A cell line or a passage strain thereof according to the present invention allows researches and experiments for clarifying the ecology of thread-sail filefish to be repeatedly conducted without using any living body of thread-sail filefish or without isolating any specific cells from a living body of thread-sail filefish. Expected researches for clarifying the ecology of thread-sail filefish include examinations of the sensitivity (infectability) of thread-sail filefish relative to infectious microorganisms such as bacteria and viruses, cytotoxicity tests for the purpose of looking into the influence of cytotoxic materials such as chemical compounds and heavy metals, tests on the responsiveness of thread-sail filefish relative to factors that can change environments, and developments of medicines and vaccines effective for treating thread-sail filefishes infected by infectious microorganisms and for preventing thread-sail filefishes from being infected by infectious microorganisms. Additionally, a cell line or a passage strain thereof according to the present invention can be expected to contribute to further development of thread-sail filefish farming techniques as a result of clarification of the ecology of thread-sail filefish.

A cell line or a passage strain thereof according to the present invention incorporates a cell line that can be cultured at a growth rate substantially equal to the growth rates of mammalian cell lines. Since such a cell line or a passage strain thereof according to the present invention can be cultured at room temperature, it can be expected to be utilized for research applications and industrial manufacturing applications as a substitute for a mammalian cell line.

MODES FOR CARRYING OUT THE INVENTION

Figure 1A:
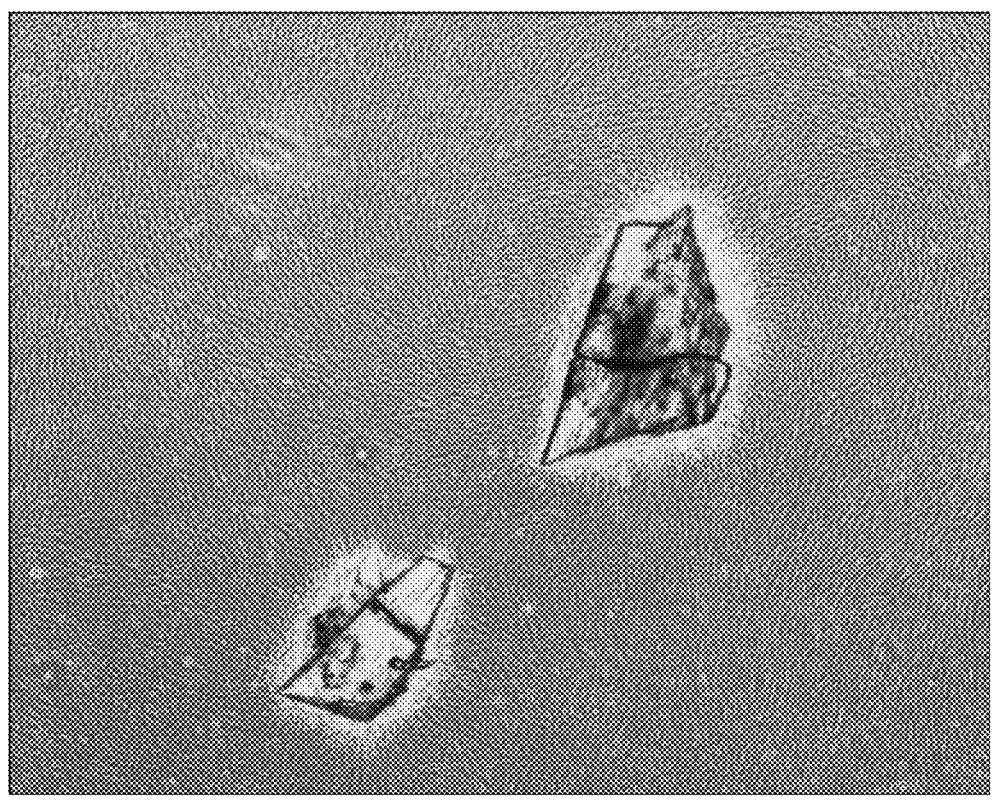
FIG. 1A is an illustration demonstrating cells migrating from a fragment of a dorsal fin of thread-sail filefish (*Stephanolepis cirrhifer*).
Figure 1B:
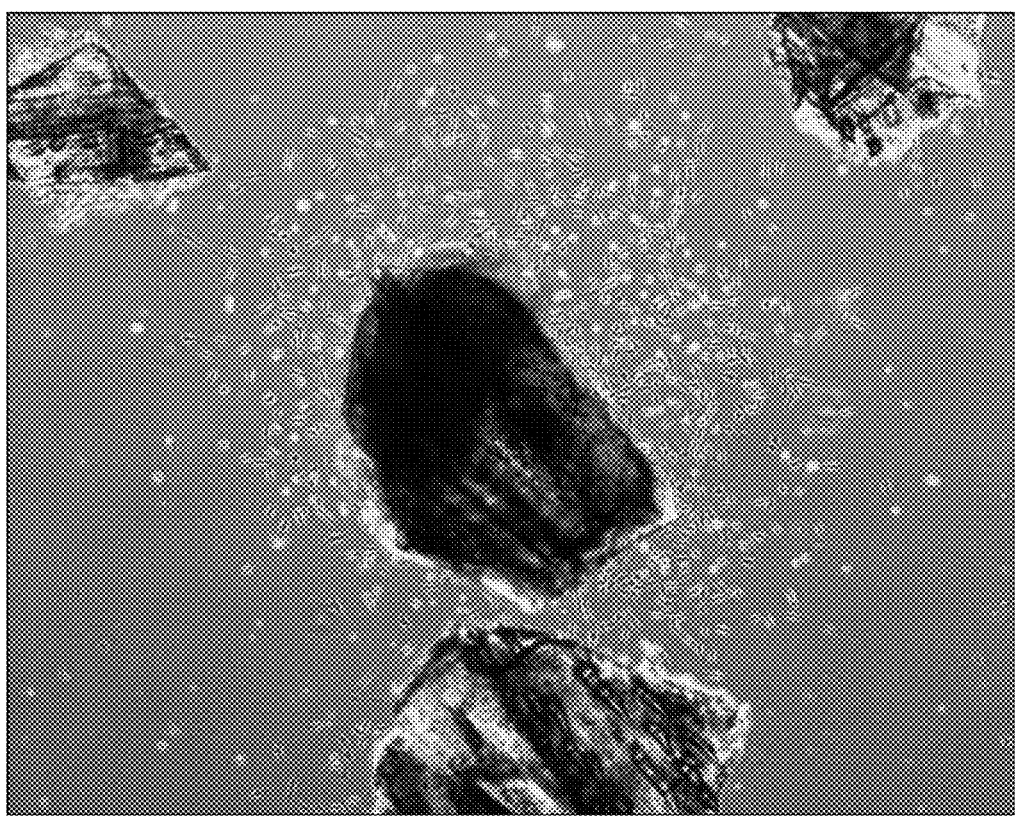
FIG. 1B is an illustration demonstrating cells migrating from a fragment of a caudal fin of thread-sail filefish (*Stephanolepis cirrhifer*).
Figure 1C:
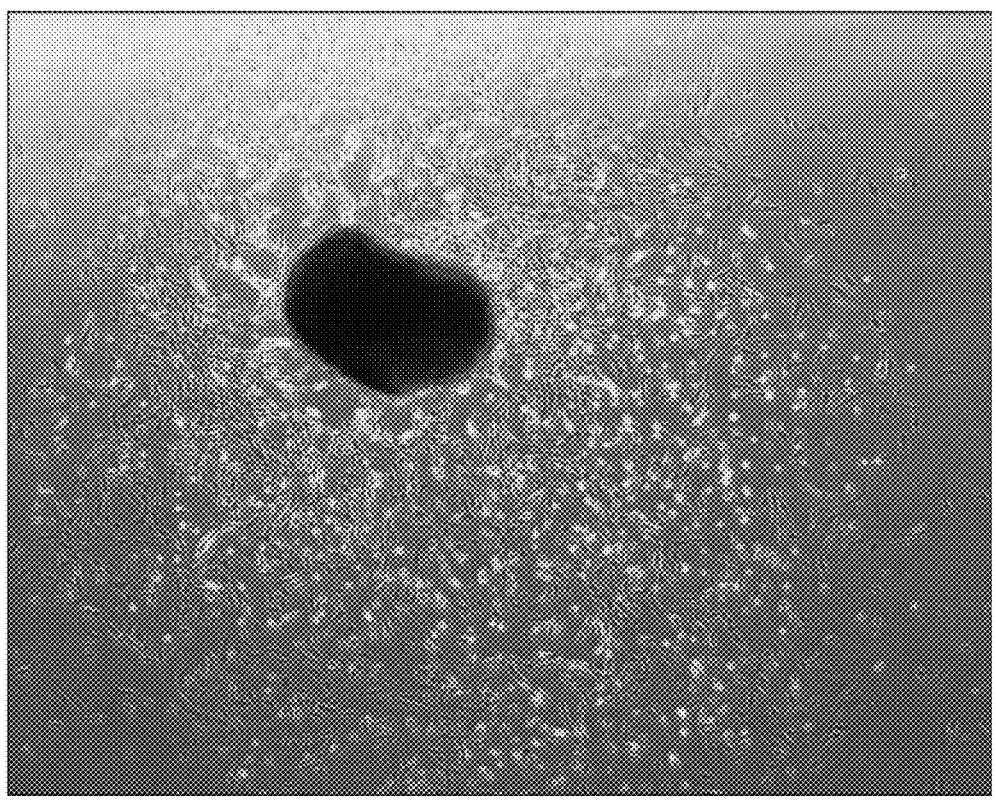
FIG. 1C is an illustration demonstrating cells migrating from a fragment of an anal fin of thread-sail filefish (*Stephanolepis cirrhifer*).
Figure 1D:
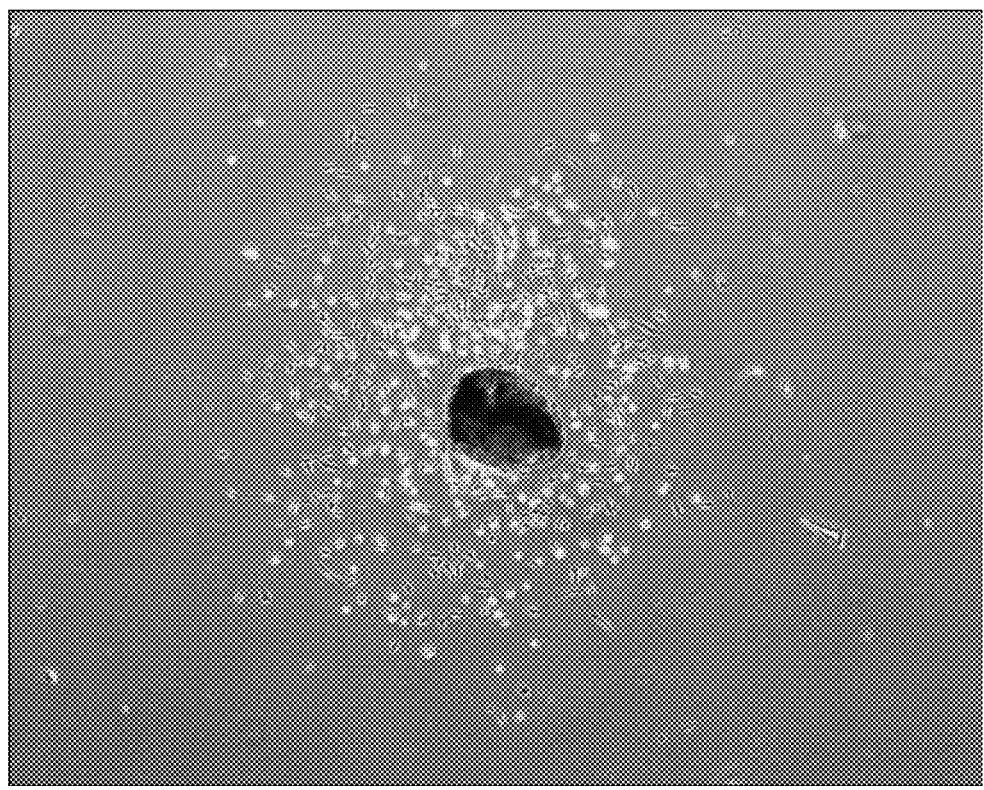
FIG. 1D is an illustration demonstrating cells migrating from a fragment of a pelvic fin of thread-sail filefish (*Stephanolepis cirrhifer*).

Hereinafter, the present invention will be described in detail.

1. First Cell Line of the Present Invention

The first cell line or the passage strain thereof according to the present invention is derived from a living body part of a fish of the family Monacanthidae.

As far as the present specification is concerned, "a cell line" has the broadest meaning that is understandable to those who are skilled in the art and is also referred to as an established cell strain or an established cell line. A cell line according to the present invention is not subjected to any particular limitations so long as it is capable of being subcultured continuously. Additionally, as far as the present specification is concerned, "a passage strain" includes all the cells obtained by subculturing a cell line. As far as the present specification is concerned, there is no rigorous discrimination between "a cell line" and "a passage strain". In other words, for the sake of convenience, cells that can be evaluated as cells that have been established are referred to as cell line and cells obtained by means of subsequently subculturing the cell line are referred to as passage strain. In the following description, cell lines and passage strains will indiscriminately are referred to as cell lines. In other words, "a cell line" may be a cell line per se or a passage strain.

The first cell line of the present invention can be prepared on the basis of the cells isolated from a living body part, which may include a tissue or an organ extracted from a fish of the family Monacanthidae. Fishes of the family Monacanthidae have a characteristic property that the skin thereof (epitheca) that covers the entire body can be peeled off with ease. For example, if the skin is partly cut by means of a kitchen knife, it then can be peeled off by hand with ease without using any particular tool. While there are no particular limitations to the fish of the family Monacanthidae from which the first cell line of the present invention is derived so long as the fish has the above-described characteristic property. Examples of such fishes include fishes of the genus *Stephanolepis*, those of the genus *Thamnaconus*, those of the genus *Cantherhines*, those of the genus *Aluterus* and those of the genus *Rudarius*. For the purpose of the present invention, specific examples of preferable fishes of the family Monacanthidae include *Stephanolepis cirrhifer*, *Thamnaconus modestus* and *Aluterus monoceros*, of which *Stephanolepis cirrhifer* is more preferable.

The living body part of a fish of the family Monacanthidae to be used to prepare the first cell line of the present invention is not limited to a specific part of the fish and may include two or more than two body parts such as tissues and organs of the fish and, furthermore, may include all the body parts of the fish. However, for the purpose of the present invention, preferable body parts of a fish of the family Monacanthidae are parts corresponding to fins. For example, preferable body parts are the fins located in the back, the chest, the abdomen, the buttock and the tail of the fish, of which the dorsal fin located in the back of the fish is more preferable.

There are no particular limitations to the method of manufacturing the first cell line of the present invention from a living body part of a fish of the family Monacanthidae and any of the methods of obtaining a cell line from a living body that are known to those who are skilled in the art can be used. For example, methods including a method of extracting a tissue or an organ from a living body, a method of isolating cells from a extracted tissue or other part of the living body, a method of obtaining primary cultured cells by culturing isolated cells and a method of obtaining a desired cell line and a passage strain thereof by subculturing primary cultured cells may be appropriately combined for manufacturing the first cell line according to the present invention.

In any of the methods that can be used for manufacturing the first cell line according to the present invention, for example, an embodiment of the step of obtaining primary cultured cells comprises the procedure as described below. Firstly, a fin part of a thread-sail filefish (*Stephanolepis cirrhifer*) is extracted from the remaining body of the fish as a square piece of an appropriate size without skinning the fish. Then, the extracted square piece is washed by an appropriate method and subsequently treated with an antibiotic substance in one to several stages, variously changing the concentration of the antibiotic substance. The treated piece is cut into micro pieces in the presence of a protease solution such as a trypsin solution in a bacteria-free environment. The above operations are conducted at low temperatures preferably in an ice-cooled condition. Then, the micro pieces that are immersed in the trypsin solution are stored and left at rest at room temperature. After the storage, the micro pieces are collected typically by centrifugation and the collected micro pieces are washed repeatedly for several times by using a culture medium that is suited for cell proliferation such as a Leibovitz's L15 culture medium in a $CO_2$ free environment. If the micro pieces are washed in a $CO_2$ environment, a standard culture medium for mammalian cells such as an RPMI1640 culture medium or an IMDM culture medium (both available from Life Technologies) can be employed. Thereafter, the micro pieces are seeded in a collagen-coated culture vessel containing a serum-containing culture medium, and made to adhere to the bottom and then they are cultured under appropriate culturing conditions, which may include a culturing temperature of 25° C., until the cultured cells cover about not less than 80% of the bottom area of the culture vessel. The cells that gather around the micro pieces are employed as primary cultured cells. Then, the culture medium in the culture vessel is removed and the cultured cells adhering to the bottom of the culture vessel are washed with an appropriate means. Subsequently, the cultured cells are removed and collected from the bottom of the culture vessel by an appropriate means, and equally divided into two or three portions, which are then subcultured in fresh culture vessels. The cells seeded in the fresh culture vessels are referred to as the first subcultured cells.

In the methods that can be used for manufacturing the first cell line according to the present invention, for example, an embodiment of the step of obtaining the first cell line of the present invention by subculturing primary cultured cells comprises the procedure as described below. Firstly, a subculturing process for obtaining the first cell line of the present invention from primary cultured cells can be conducted by using a serum-containing culture medium in appropriate culturing conditions as in the above-described step of obtaining primary cultured cells. The number of cells per unit volume at the time of starting the subculturing may be $4 \times 10^5$ cells/ml and the time of finishing the subculturing may be, for example, the time when the cells become confluent by not less than 90%, while the culture medium may need to be replaced when the culture solution is contaminated by dead cells, although the above passages do not constitute any limitative requirements.

The first cell line of the present invention can be stored and grown by any of conventional methods that are known to those who are skilled in the art, although there are no particular limitations to the method to be used for storing and growing the first cell line of the present invention. As a method of cryopreserving the first cell line of the present invention, for example, after adding a commercially available culture medium to the cell line, the cells are collected typically by centrifugation and then a commercially available cryopreservation solution for serum-free cultured cells can be added to the collected cells to achieve cryopreservation of the cells. The frozen cell line of the present invention can be thawed into a semi-thawed state at room temperature and then completely thawed by replacing the culture medium with fresh serum-free culture medium for an appropriate number of times. The subculturing process as described above can be conducted by adding a serum-containing culture medium to the thawed cells.

There are no particular limitations to the method of determining that the first cell line of the present invention has been manufactured. For example, primary cultured cells may be subjected to being subcultured for not less than 30 times, preferably not less than 50 times, more preferably not less than 70 times and further preferably not less than 100 times and then it will be possible to determine the first cell line of the present invention by observing the cells obtained after the subculturing operations.

There are no particular limitations to the first cell line of the present invention provided that it is a cell line that is capable of being subcultured continuously. The first cell line of the present invention preferably is capable of being subcultured substantially limitlessly. More specifically, in an embodiment of the first cell line of the present invention, the first cell line can be cultured repeatedly over generations when appropriate attention and techniques are exerted to a level that those who are skilled in the art can normally achieve by following the above-described subculturing methods.

The first cell line of the present invention can possess various properties and it preferably appears morphologically like a fibroblast. A fibroblast cell shows a morphologically particular form that is characterized by a flat and oblong external morphology, frequently observable irregular projections and an elliptical nucleus. When the first cell line of the present invention appears morphologically like a fibroblast, it preferably at least shows a flat and oblong external morphology, although there are no particular limitations to the morphology of the first cell line of the present invention provided that it has any one of morphological characteristics specific to fibroblast. If the first cell line of the present invention appears morphologically like a fibroblast or not can be confirmed by any of various techniques that are known to those who are skilled in the art and can be used for observing the morphologies of cells. For example, it can be confirmed by observing the first cell line of the present invention through an optical microscope set to an appropriate magnification.

When the first cell line of the present invention can be subcultured substantially limitlessly, for example, it can undergo cell divisions for not less than 30 times, preferably not less than 50 times, more preferably not less than 70 times and further preferably not less than 100 times. In instances where the first cell line of the present invention can undergo such cell divisions, the first cell line of the present invention can be regarded as immortalized cell line. If the first cell line of the present invention can be subcultured substantially limitlessly or not can be determined by, for example, subculturing the cell line of the present invention in the above-described manner and confirming that the passage number reaches the above-described number.

As is known to those who are skilled in the art, the doubling time refers to the time required for the number of cells to become twice of the original number. The doubling time accords with the cell cycle in principle for cells in a proliferation phase. While there are no particular limitations to the method of measuring the doubling time of the first cell line of the present invention, for example, when the first cell line is subcultured in the above-described manner, namely when the first cell line is cultured at 25° C. by using a Leibovitz's L-15 culture medium that contains FBS by 10%, the doubling time can be determined by counting the number of cells in the proliferation phase at 2 to several points, preferably at not less than 3 points.

There are no particular limitations to the doubling time of the first cell line of the present invention. For example, when the initial cell number is about $1.0 \times 10^6$ cells/ml, preferably 0.1 to $1.5 \times 10^6$ cells/ml, more preferably 0.4 to $1.0 \times 10^6$ cells/ml and the first cell line is cultured in a culture vessel having a bottom area of 75 cm$^2$, using Leibovitz's L-15 culture medium containing FBS by 10%, at 25° C. in the absence of $CO^2$, the doubling time is shorter than that of primary cultured cells and preferably between 10 and 48 hours, more preferably between 12 and 36 hours, more preferably between 14 and 28 hours, further preferably between 16 and 24 hours and particularly preferably about 18 hours. While there are not particular limitations to the methods of determining the doubling time from the initial number of cells, for example, the methods include a method of determining the doubling time on the basis of the number of cells counted with the use of a cell number counting instrument such as TC10 Automated Cell Counter (available from Bio Rad), using software for determining the increase of cell number per unit time from points of observation (time) and cell numbers (http://www.doubling-time.com/compute.php?lang=en) may be employed. Additionally, the number of cells can be measured, for example, by in advance attaching an indicator (marker) to the bottom of the culture vessel, culturing the first cell line of the present invention, and then filming and counting the number of cells around the marker through an inverted routine microscope. At this time, the number of cells in each of the squares (e.g., 1 mm×1 mm squares) formed by the reticle on the eyepiece of the microscope may be counted and the numbers of cells in the squares may be averaged to determine the number of cells per unit area. A cell growth curve is obtained by observing the cells that are being cultured over a predetermined period of time. The growth cycle including the lag phase, the log phase, the stationary phase and the death phase in the growth period of a cell can be informed from the growth curve. The time required to double the number of cells in the log phase (doubling time) can be determined by the calculation formula shown below.

$$\text{doubling time} = (t - t_0) \log 2 / (\log N - \log N_0)$$

t: time [h], N: number of cells at time t $t_0$: initial time [h], $N_0$: number of cells at time $t_0$ As cells are cultured in a culture vessel in a state where the cells are made to adhere to the bottom surface of the culture vessel, the cultured cells normally stop growing when they become confluent to the extent of covering the entire bottom surface. In other words, the cultured cells can grow until they form a single layer of cells on the bottom surface of the culture vessel. However, an embodiment of the first cell line of the present invention can keep on growing after they form a single layer of cells to form another cell layer on the first single cell layer, preferably can be cultured so as to form a multilayer structure. Thus, the first cell line of the present invention may incorporate a cell line that can be cultured so as to form a three-dimensional structure where cell layers are piled up to one another. That the first cell line of the present invention can form a multilayer structure can be proved by culturing the first cell line of the present invention after it becomes confluent and observing the structure of the cultured cells by means of any of the techniques known to those who are skilled in the art. There are no particular limitations to the multilayer structure formed by the first cell line of the present invention so long as it has at least an additional cell layer formed on an initial single cell layer. The multilayer structure has two layers, or three or more layers.

There are no particular limitations to the number of chromosomes in the first cell line of the present invention because it varies depending on the genus and the gender of the fish of the family Monacanthidae from which the first cell line is derived. When, for example, the first cell line is derived from the dorsal fin of a female thread-sail filefish (*Stephanolepis cirrhifer*), the number of chromosomes can be 66, 33 or 32. There are instances where the first cell line of the present invention can be regarded as a single independent cell or a group of cells. In the instance where the first cell line can be regarded as a group of cells and is derived from the dorsal fin of a female thread-sail filefish (*Stephanolepis cirrhifer*), the first cell line of the present invention can be a group of cell lines, each of which has a number of chromosomes that is equal to 66, 33 or 32. If such is the case, the first cell line of the present invention is a group of cell lines, each of which has a number of chromosomes that is preferably in accordance with the frequency distribution having a maximum value of 66, a minimum value of 32 and a mode of 33. More preferable, the first cell line of the present invention is a group of cell lines wherein the frequency of 33 chromosomes of the mode is about 90% of all the frequencies in the frequency distribution. There are no particular limitations to the method of analyzing the number of chromosomes of the first cell line of the present invention and any of the methods known to those who are skilled in the art can be adopted for the purpose of the present invention. For example, the number of chromosomes can be analyzed by the method used in Examples, which will be described hereinafter.

As a specific example, the first cell line of the present invention is derived from a living body part of a fish of the family Monacanthidae and has not less than one of properties (1) through (5) listed below. Preferably, the first cell line has property (1) listed below and not less than one of properties (2) through (5) also listed below. More preferably, the first cell line has properties (1) and (2) listed below and not less than one of properties (3) through (5) also listed below. Further preferably, the first cell line has properties (1) through (3) listed below and either or both of properties (4) and (5) also listed below. Particularly preferably, the first cell line has all properties (1) through (5) listed below:

(1) a property of being capable of being subcultured substantially without limitations.

(2) a property of being similar to fibroblast in morphology.

(3) a property of being able to be cultured to form a multilayer structure.

(4) a property of having a number of chromosomes that is in accordance with the frequency distribution having a maximum value of 66, a minimum value of 32 and a mode of 33, the frequency of 33 chromosomes of the mode preferably taking about 90% of all the frequencies in the frequency distribution.

(5) a property of showing a doubling lime of about 14 to 28 hours when the cell line or the passage strain thereof is cultured in a culture vessel having a bottom area of 75 cm², using a Leibovitz's L-15 culture medium containing FBS by 10%, at 25° C. in the absence of $CO_2$ with an initial cell number of about $1.0 \times 10^6$ cells/ml.

2. Second Cell Line of the Present Invention

In another mode of cell line of the present invention, there is provided the second cell line or the passage strain thereof that derived from a living body part of a fish of the family Monacanthidae and for which at least a cell marker selected from a group consisting of TRA-1-60, OCT4 and SSEA-3 is positive. The second cell line of the present invention can be manufactured from a living body part of a fish of the family Monacanthidae by means of a method similar to the method of manufacturing the first cell line of the present invention. The second cell line of the present invention preferably appears morphologically like a fibroblast.

The cell lines that are positive for SSEA-3 or TRA-1-60, OCT4, refer to cell lines expressing the epitopes recognized respectively by anti-human TRA-1-60 Antibody, anti-human SSEA-3 Antibody and anti-human OCT4 Antibody.

It is known that anti-TRA-1-60 Antibody reacts with the protein (epitope) expressed in undifferentiated human embryonic stem (ES) cells, embryonic carcinoma (EC) cells and embryonic germ (EG) cells, and the epitope is lost upon cell differentiations. It is believed that OCT4 is a transcription factor that is highly expressed in ES cells and is involved in maintaining the undifferentiating property of ES cells and also maintaining multipotency. SSEA-3 is known as cell marker for pluripotent stem cells such as ES cells. The gene sequences encoding TRA-1-60, OCT4 and SSEA-3 are registered, for example, by GenBank, which is a public data base of National Center for Biotechnology Information (NCBI), with respective ACCESSION numbers of NM_001018111 or NM_005397 for TRA-1-60, NM_002701 for OCT4 and NM_033149 for SSEA-3 (ACCESSION number of amino acid sequence being Q9J167).

TRA-1-60, OCT4 and SSEA-3 are cell markers for indicating pluripotency. They are commonly characterized in that they are not found the surfaces of cells after differentiation. On the basis of this fact, cell lines for which one, two or all of cell markers IRA-1-60, OCT4 and SSEA-3 are positive can be presumed to have pluripotency or the ability of differentiating into various different cells. Therefore, the second cell line of the present invention is highly probably a pluripotent cell, line. The term of "pluripotency" as used herein should not be limitatively interpreted and includes the meaning of totipotency in addition to the academic meaning of pluripotency (multpotency). In other words, the term of "pluripotency" as used herein can be interpreted to include not only pluripotency and totipotency but also probability of pluripotency or totipotency. Differently stated, the term of "pluripotency" as used herein encompasses the broadest meaning of the word.

That at least a cell marker selected from a group of cell markers consisting of TRA-1-60, OCT4 and SSEA-3 is positive with respect to a cell line can be confirmed by applying any of the techniques of looking into a specific cell marker that are known to those who are skilled in the art. For example, an immunochemical technique can be employed to confirm the positivity by following the procedure as described below. Namely, cultured cells are fixed to the bottom of a culture vessel and subjected to a blocking treatment, and then a primary antibody against TRA-1-60, OCT4 or SSEA-3 is added to them to cause a primary antibody reaction to take place. Then, after removing the unreacted part of the primary antibody, a fluorescence-labelled secondary antibody against the primary antibody is added to cause a secondary antibody reaction to take place. Subsequently, after removing the unreacted part of the secondary antibody, the cells that are positive for TRA-1-60, OCT-4 or SSEA-3 can be confirmed by observing the fluorescence-labelled cells. While cells that are positive for TRA-1-60, OCT4 or SSEA-3 can be confirmed by way of a single operation or a couple of operations by appropriately changing the structure of the primary antibody (globulin type, fragmented structure or the like), the recognition specificity of the primary antibody relative to the secondary antibody, the waveform of the fluorescent label and so on, it is preferable to divide the cells into three groups and confirm that the three groups of cells are positive respectively for TRA-1-60, OCT4 and SSEA-3. Additionally, the second cell line of the present invention can express cell makers other than TRA-1-60, OCT4 and SSEA-3 that are specifically expressed in pluripotent stem cells.

The second cell line of the present invention has little affinity for anti-human NANOG antibody and therefore can be said to be weakly positive or substantially negative relative to NANOG depending on the conditions of the background and the employed image processing technique.

Since the second cell line of the present invention expresses any of the above-listed cell markers, it is highly probably a pluripotent cell line. Therefore, an embodiment of the second cell line of the present invention is a cell line having an ability of differentiating into cells including, for example, muscle cells, muscle cell-like cells, epithelial cells, epithelial cell-like cells, nerve cells, nerve cell-like cells, adipocytes, adipocyte-like cells, hepatocytes and hepatocyte-like cells.

For the purpose of the present invention, differentiation of a cell means not only disappearance of the expression of at least a type of cell marker selected from a group of cell markers consisting of TRA-1-60, OCT4 and SEEA-3 and expression of a cell marker that is specific to differentiated cell but also a simple morphological change of cell. A muscle-like cell, an epithelial cell-like cell, a nerve cell-like cell, an adipocyte-like cell and a hepatocyte-like cell as used herein can include a cell that is, for example, not completely differentiated into a muscle cell or another cell but a cell on the way of differentiation into a muscle cell or another cell and a cell that appears morphologically like a cell differentiated into a muscle cell or another cell, whichever appropriate.

A preferable embodiment of the second cell line of the present invention is able to differentiate into a type of cells, preferably into not less than two types of cells, more preferably into not less than three types of cells, further preferably into not less than four types of cells selected from a group consisting of a muscle cell, a muscle cell-like cell, an epithelial cell, an epithelial cell-like cell, a nerve cell, a nerve cell-like cell, an adipocyte, an adipocyte-like cell, an immune cell, an immune cell-like cell, a hepatocyte and a hepatocyte-like cell. The above-listed differentiated cells are only cited as examples and the second cell line of the present invention encompasses cell lines that are capable of differentiating into one or more than one types of cells other than the above-listed ones.

The second cell line of the present invention can be differentiated into various cells by means of any of the techniques of differentiating pluripotent cells into various cells known to those who are skilled in the art. For example, a technique of selecting conditions such as the presence or absence and the type of coating on the culture vessel, presence or absence and the type of serum and the type of culture medium can be used to achieve such differentiations. Thus, for instance, a muscle cell, a muscle cell-like cell, an epithelial cell, an epithelial cell-like cell, a nerve cell, a nerve cell-like cell, a hepatocyte, a hepatocyte-like cell, a fibrocyte, a fibrocyte-like cell, an adipocyte, an adipocyte-like cell, an immune cell and an immune cell-like cell can be obtained from the second cell line of the present invention as shown in FIGS. 10B through H.

Figure 10A:
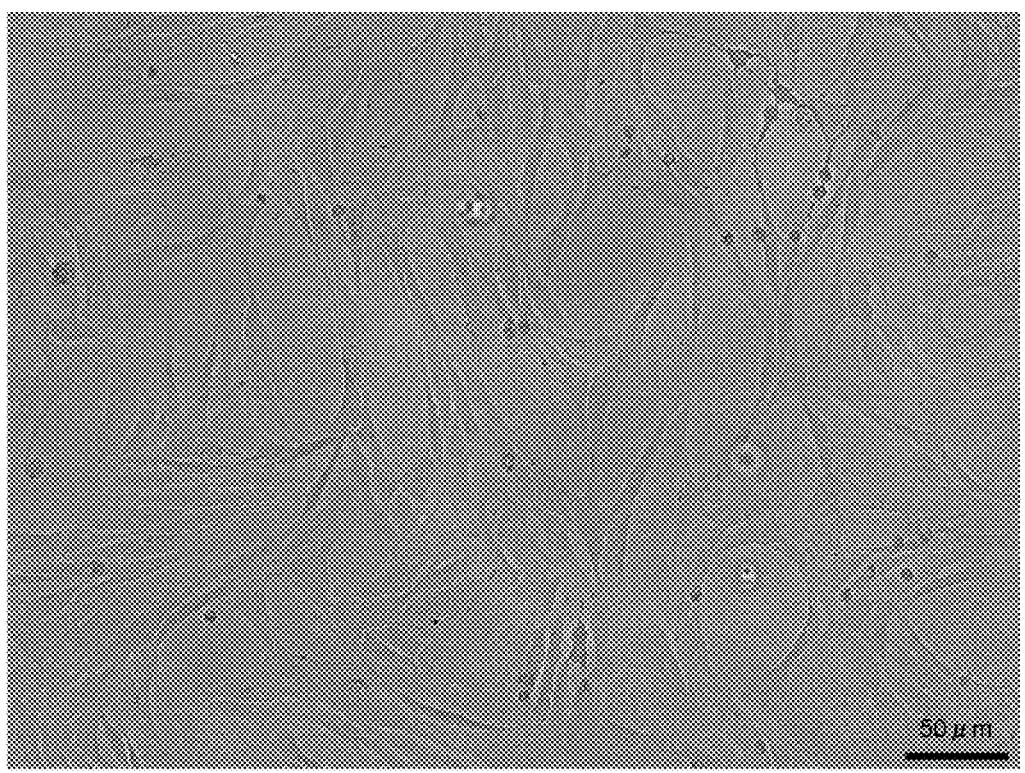
FIG. 10A is an illustration demonstrating that KSC cells appeared like fibroblasts.
Figure 10B:
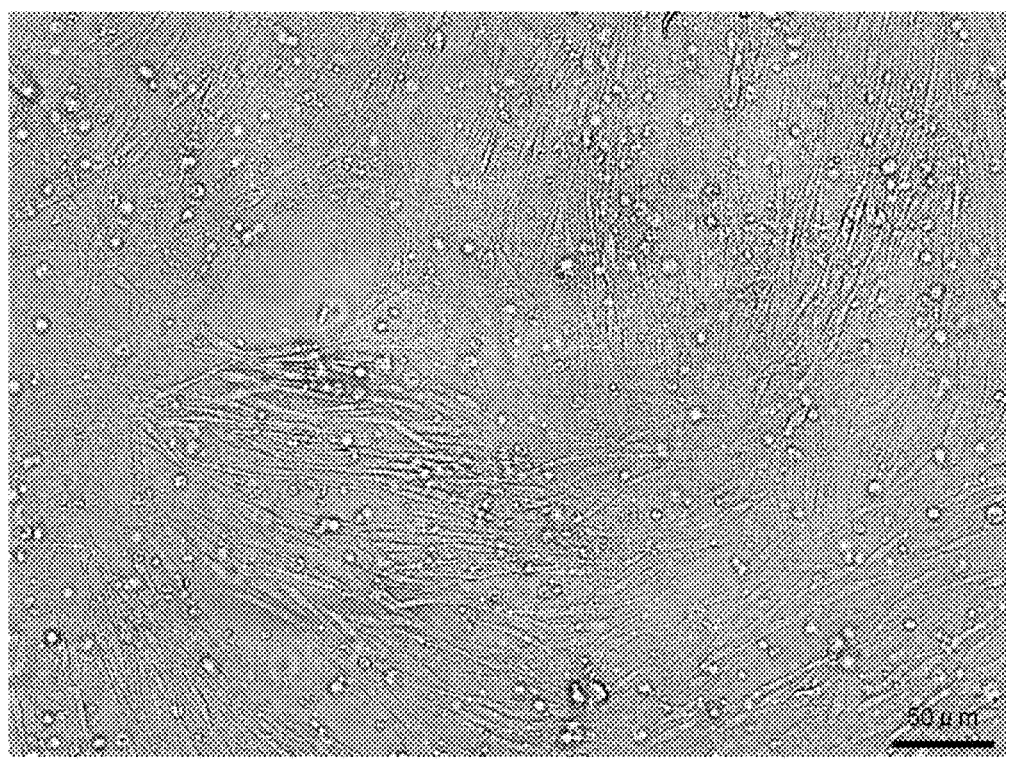
FIG. 10B is an illustration demonstrating that KSC cells were differentiated into cells that appeared like muscle cells.
Figure 10C:
FIG. 10C is an illustration demonstrating that KSC cells were differentiated into cells that appeared like epithelial cells.
Figure 10D:
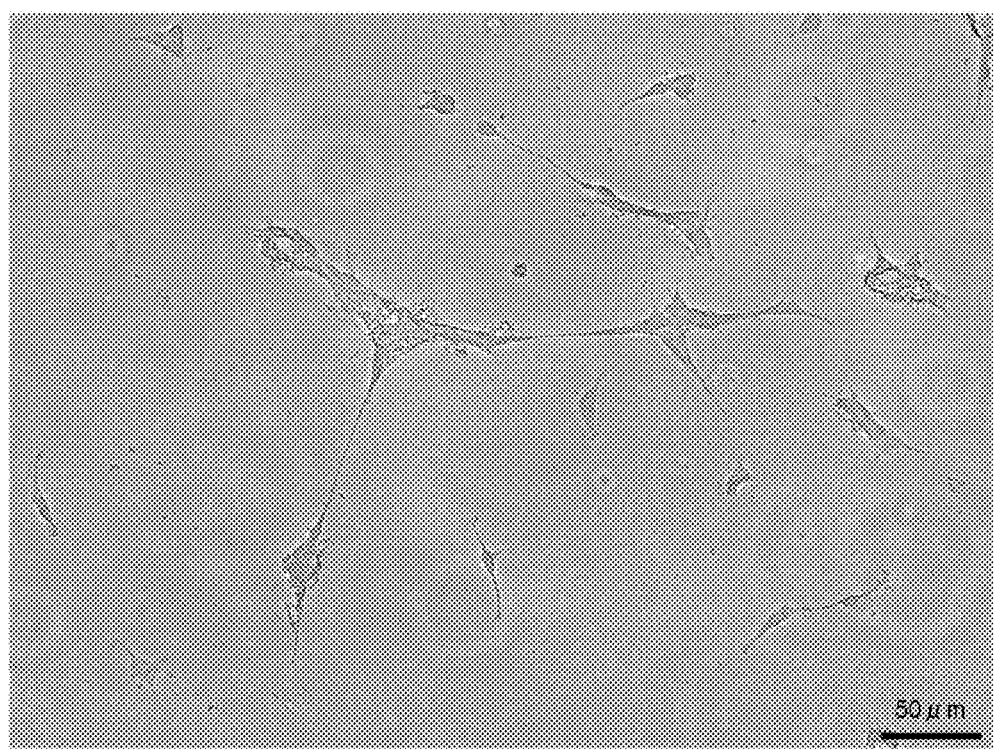
FIG. 10D is an illustration demonstrating that KSC cells were differentiated into cells that appeared like nerve cells.
Figure 10E:
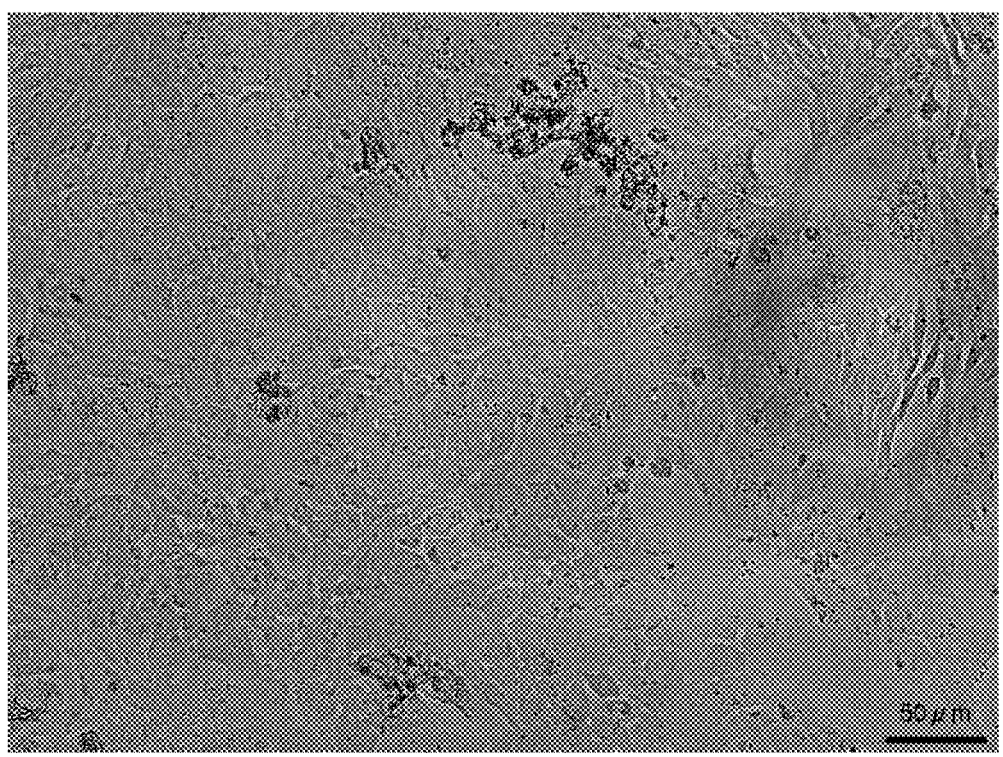
FIG. 10E is an illustration demonstrating that KSC cells were differentiated into cells that appeared like hepatocytes.
Figure 10F:
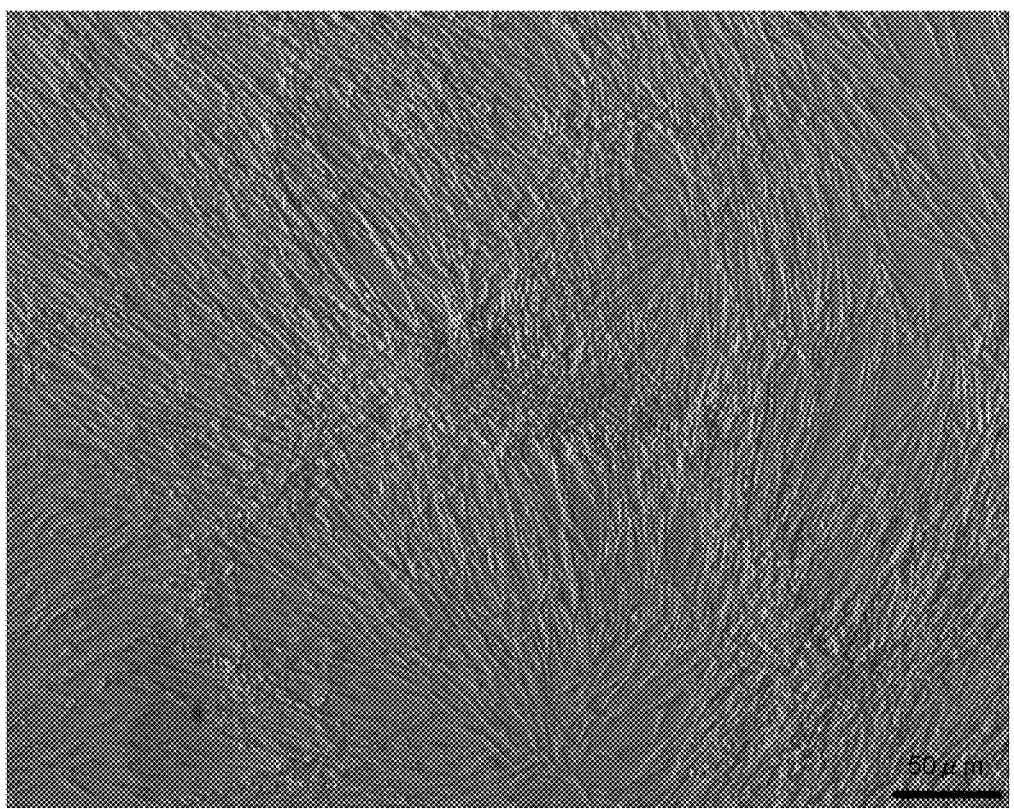
FIG. 10F is an illustration demonstrating that KSC cells were differentiated into cells that appeared like fibrocytes.
Figure 10G:
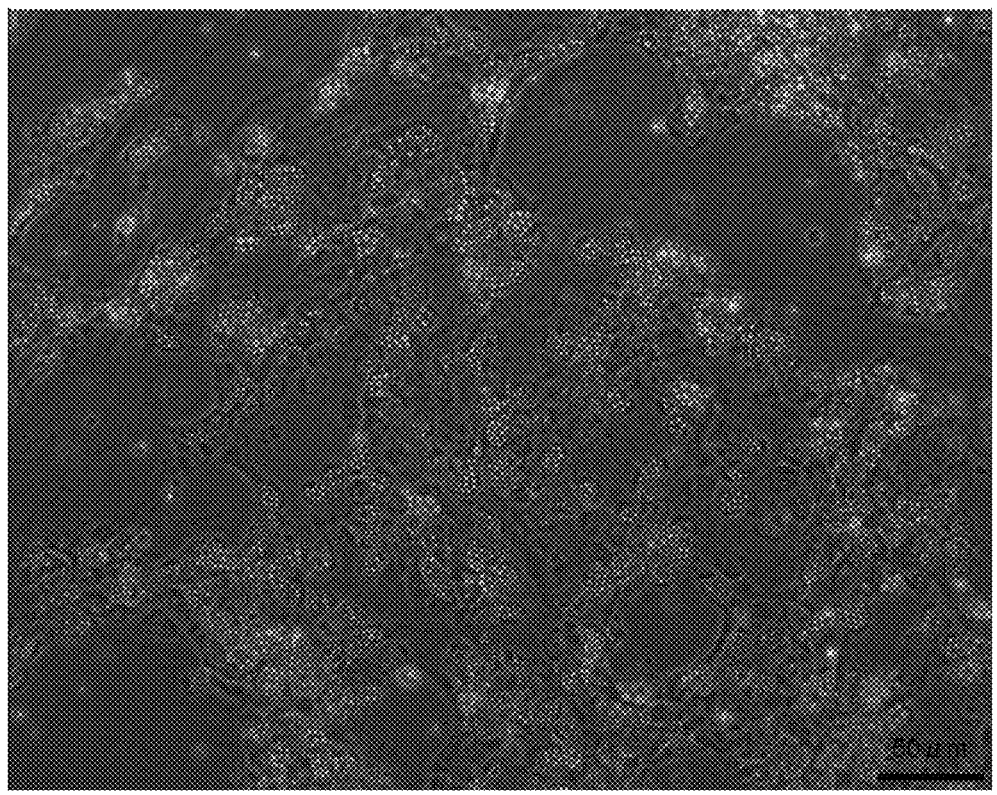
FIG. 10G is an illustration demonstrating that KSC cells were differentiated into cells that appeared like adipocytes.
Figure 10H:
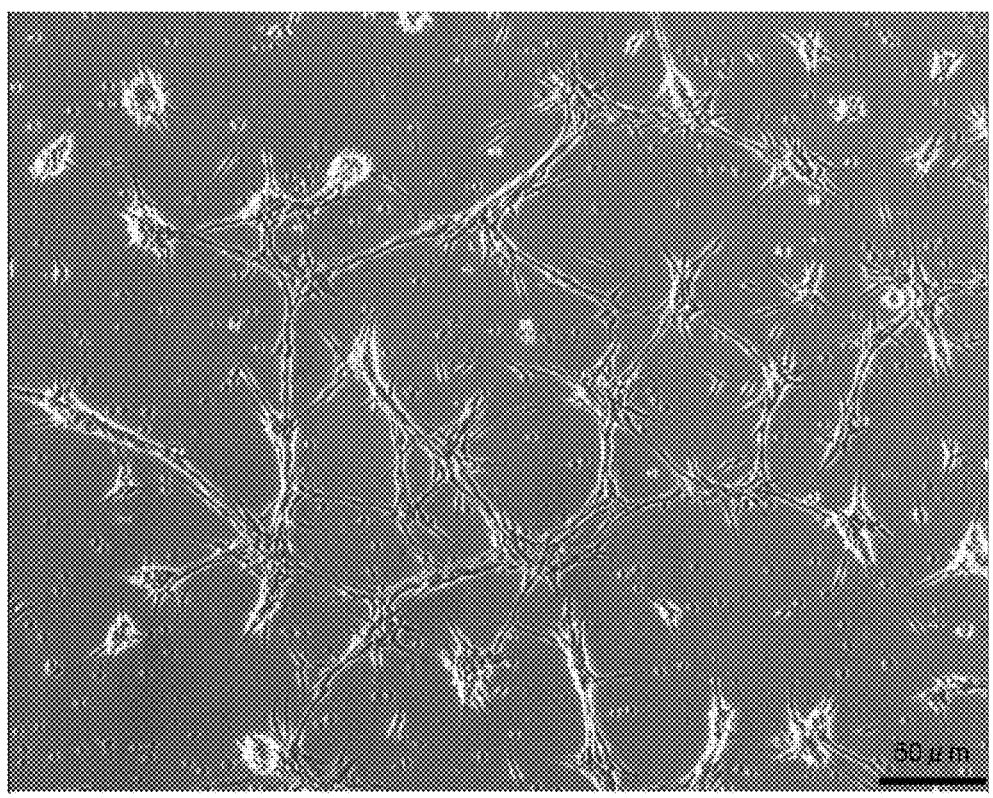
FIG. 10H is an illustration demonstrating that KSC cells were differentiated into cells that appeared like branches of a rose tree and which may possibly be immune cells.
Figure 10I:
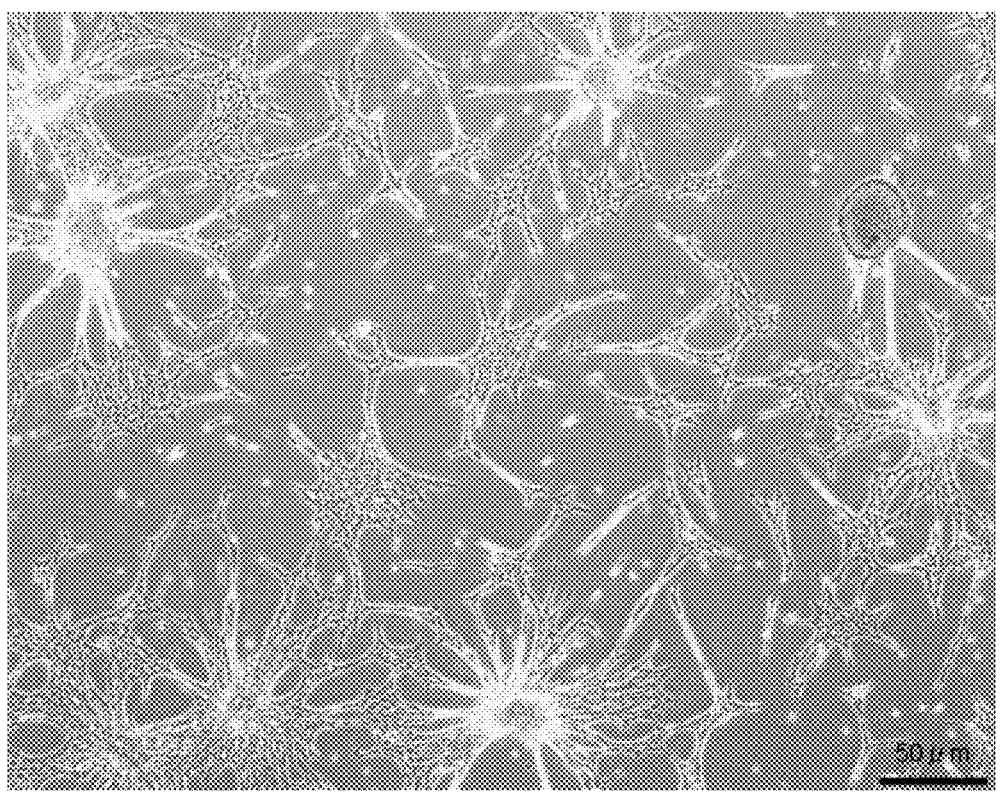
FIG. 10I is an illustration demonstrating that KSC cells were differentiated into cells that appeared like huge cocoons.
Figure 11A:
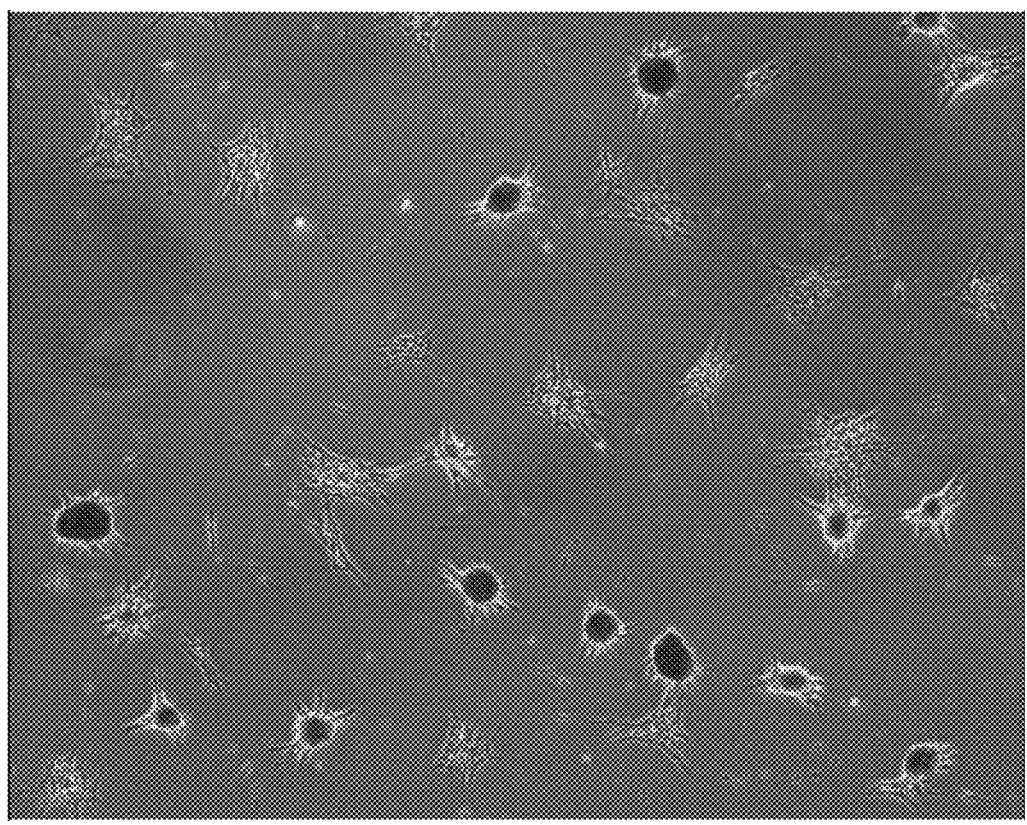
FIG. 11A is an illustration demonstrating that the huge cocoon-like fused cells, which were induced from KSC cells, were positive for alkaline phosphatase activity, which is a cell marker specific to undifferentiated cells.
Figure 11B:
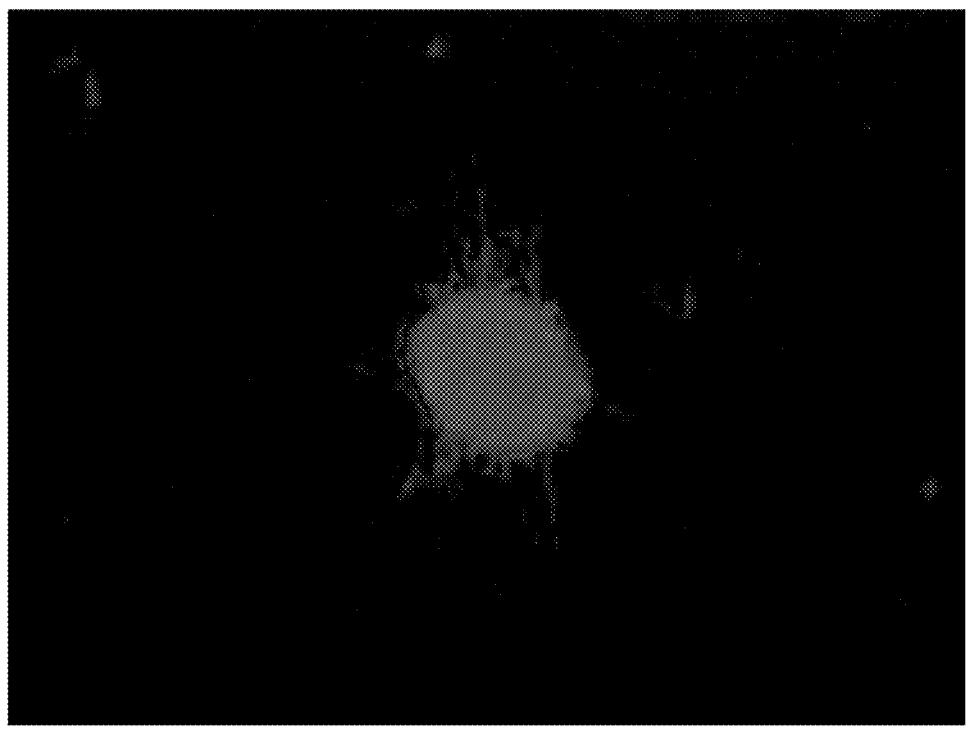
FIG. 11B is an illustration demonstrating that the huge cocoon-like fused cells, which were induced from KSC cells, were positive for NANOG, which is a cell marker specific to undifferentiated cells.
Figure 11C:
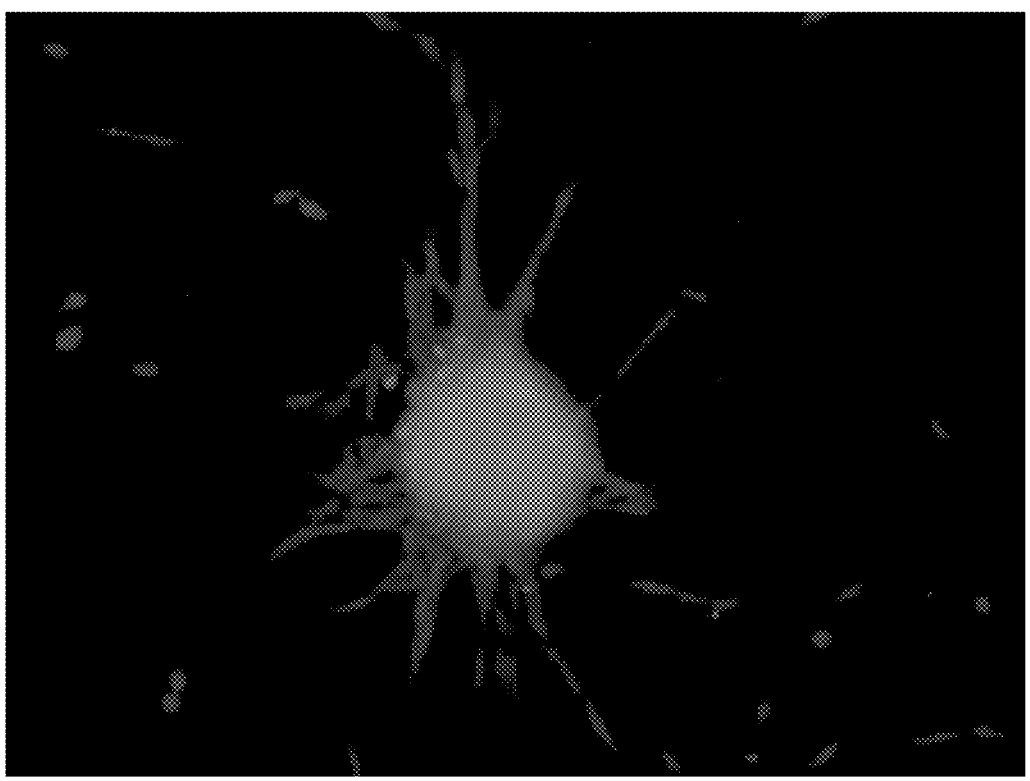
FIG. 11c is an illustration demonstrating that the huge cocoon-like fused cells, which were induced from KSC cells, were positive for TRA-1-60, which is a cell marker specific to undifferentiated cells.
Figure 11D:
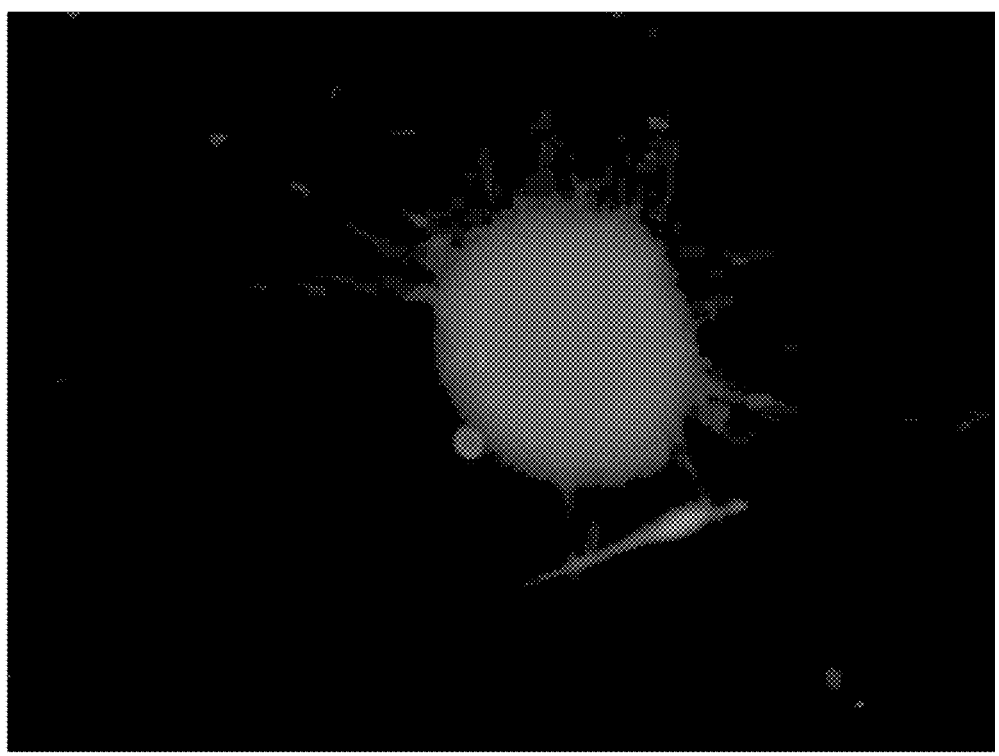
FIG. 11D is an illustration demonstrating that the huge cocoon-like fused cells, which were induced from KSC cells, were positive for OCT4, which is a cell marker specific to undifferentiated cells.
Figure 11E:
FIG. 11E is an illustration demonstrating that the huge cocoon-like fused cells, which were induced from KSC cells, were positive for SSEA-3, which is a cell marker specific to undifferentiated cells.

Among the above cells, the cells shown in FIG. 10B are muscle cell-like cells that have an oblong and spindle-like or fiber-like morphology and a proliferative potency. The cells shown in FIG. 10C are epithelial cell-like cells, each having a flat morphology whose periphery is undefinable, and growing into a dense population. The cells shown in FIG. 10D are nerve cell-like cells that have a cell morphology with extendible axons or dentrites but do not have any proliferative potency. The cells shown in FIG. 10E are hepatocyte-like cells that appear to have something like fat droplets in the inside of cytoplasm, each being finitely cable of dividing into two or more than two cells. The cells shown in FIG. 10F are fibrocyte-like cells that have a fiber-like shape similar to or more than muscle cells and have proliferative potency. The cells shown in FIG. 10G are adipocyte-like cells, each having many cavities in the inside, some of which have a cell morphology with extendible axons but do not have any proliferative potency. The cells shown in FIG. 10H are immune cell-like cells that appear like branches of a rose tree and have extendible projections with pointed tips but do not have any proliferative potency, the cells linking themselves with adjacent ones. As shown in FIG. 10I, fused cells forming a huge cocoon-like structure that is produced as a result of fusions of cells that can expand like rubber and have proliferative potency can be obtained from the second cell line of the present invention. The fused cells are positive for alkaline phosphatase activity as shown in FIG. 11A and positive for NANOG as shown in FIG. 11B. Furthermore, the fused cells are also positive for TRA-1-60, OCT4 and SSEA-3 as shown respectively in FIGS. 11C through 11E. In addition to the gene sequences respectively encoding TRA-1-60, OCT4 and SSEA-3 above, for example, NANOG is registered with ACCESSION number of NM_024865 by GenBank that is a public database of NCBI.

Whether a cell line has already differentiated can be evaluated by confirming a morphological changing found by comparing the morphological appearance of the cell line with the fibroblast-like morphological appearance that is observed at the time of being subcultured, for example, the morphological appearance as shown in FIG. 10A and also by any of the differentiated cell determining techniques that are known to those who are skilled in the art. For instance, the differentiation of a cell line can be confirmed by using as indicator a cell marker for each differentiated cell, or the substance that each differentiated cell produces.

In another aspect of the present invention, there is provided a method of manufacturing a differentiated cell from the second cell line of the present invention. Thus, a method of manufacturing a differentiated cell according to the present invention comprises a step of culturing the second cell line of the present invention in a culture vessel coated or not coated at the bottom surface thereof with cell adhesion molecules, using a culture medium for mammalian cells, a culture medium for fish cells or a culture medium for insect cells not containing any serum or containing mammalian serum, fish serum or a serum replacement.

In still another aspect of the present invention, there is provided a kit for manufacturing a differentiated cell comprising the second cell line of the present invention. A kit for manufacturing a differentiated cell according to the present invention preferably comprises serum, a culture medium and a culture vessel. More preferably, a kit for manufacturing a differentiated cell according to the present invention further comprises a buffer and a pH adjusting agent. Since the second cell line of the present invention can differentiate into cells other than the above-cited differentiated cells, there are no particular limitations to the serum, the culture medium, the culture vessel, the buffer and the pH adjusting agent comprised in a kit according to the present invention and they may appropriately be selected from various candidate components for such a kit.

For example, the serum that is comprised in a kit for manufacturing differentiated cells according to the present invention may be mammalian serum, fish serum or a serum replacement. The serum employed can be selected from fetal bovine serum (Gibco; No. 26140-087 etc.), horses serum (Gibco; No, 16050-130 etc.), goat serum (Gibco; No. 16210-064 etc.), rabbit serum (Gibco; No. 16120-099 etc.), mouse (KAC; No. AS3054 etc.), chicken serum (Gibco; No. 16110-082 etc.), lamb serum (Gibco; No. 16070-096 etc.), pig serum (Gibco; No. 26250-084 etc.), dog serum (KAC; No. A53070 etc.), monkey serum (FNIC; No. A33076 etc.) and salmon serum SeaGrow (East Cost. Bio; JJ80-N2751 etc.) as well as serum of other fishes such as sea bream and yellow tail. A kit for manufacturing differentiated cells according to the present invention may comprise a type of serum, or two or more than two types of serum. There are no particular limitations to the method of obtaining serum for the purpose of the present invention. In other words, commercially available serum may be used for the purpose of the present invention.

A serum replacement can be used as serum that a kit for manufacturing differentiated cells according to the present invention comprises. Examples of serum replacements that can be used for the purpose of the present invention include Knockout (registered trademark) Serum Replacement (KSR), lactalbumin hydrolyte, additive for culture media for culturing fish-derived cells Hy-Fish (Maruhachi Muramatsu), Nu-Serum (BD; No. BSE 355100), SERUM PLUS (Sigma; No. 14008C-500ML) and L-Glutamine solution (Sigma; No. 59202C-100ML). One or more of these serum replacements can be used for a kit for manufacturing a differentiated cell according to the present invention.

The culture medium that a kit for manufacturing a differentiated cell according to the present invention comprises may be selected from, for example, L-15 (Gibco; No. 11415-064), AIM V (Life Technologies; No. 087-0112DK), IMDM (Gibco; No. 12440-053), RPMI (Gibco; No. 11835030), EX-CELL 420 with L-glutamine (Nichirei; No. 14420C, for insects), D-MEM (Gibco), mTeSR1 (Stem Cell; No. ST-05850, for stem cells), Ham's F-12 (Gibco; No. 11765-054) and Culture Medium for Primate ES/iPS cells (ReproCELL; No. RCHEMD001). One or more of these culture media can be used for a kit for manufacturing a differentiated cell according to the present invention.

A kit for manufacturing a differentiated cell according to the present invention may further comprise a growth factor and a culture medium additive as components in addition to a culture medium. Examples of growth factors and culture medium additives include epithelial cell growth factors, fibroblast growth factors, nerve growth factors, insulin-like growth factors, platelet-derived growth factors, vascular endothelial cell growth factors, transforming growth factors, cytokines, stem cell factors, T-STIM culture additive, IL-3 culture supplement, vascular endothelial cell growth supplements, MITO+Shiramu extenders and ITS culture additives. One or more of these growth factors and culture medium additives can be used for the purpose of the present invention. There are no particular limitations to the method of obtaining growth factors and culture medium additives and any of growth factors and culture medium additives that are commercially available may be used. Commercially available growth factors and culture medium additives that can be used for the purpose of the present invention include, for example, those available from Nippon Becton Dickinson Company LTD. (BD; http://www.bdj.co.jp/falcon/products/1f3pro00000c64gx.html, the entire contents of which are incorporated herein by reference for the purpose of supporting the disclosure of the present invention).

The culture vessel that a kit for producing a differentiated cell according to the present invention comprises is preferably a culture vessel coated at the bottom surface hereof with cell adhesion molecules such as molecules of collagen, fibronectin, laminin, poly-D-lysine, poly-L-lysine, gelatin or streptavidin or a culture vessel whose bottom surface is not coated with any cell adhesion molecules. Preferably two or more than two types of culture vessels may be used for the purpose of the present invention. There are no particular limitations to the method of obtaining a culture vessel whose bottom surface is coated with cell adhesion molecules. In other words, one or more than one commercially available culture vessels may be used. Alternatively, one or more than one culture vessels whose bottom surfaces are not coated and cell adhesion molecules may be brought in separately and the culture vessel or vessels may be coated at the bottom surface with cell, adhesion molecules with a technique known to those who are skilled in the art. There are no particular limitations to the method of obtaining cell adhesion molecules. Examples of commercially available cell adhesion molecules including molecules of collagen such as collagen I (Thermo: 132706) or IV collagen (Cosmo Bio 354534), poly-D-lysine (Thermo: 32703); gelatin (CR: 354654); fibronectin (BD: 356242); poly-L-lysine (Thermo), poly-L-ornithine (Bio Coat); laminin (BD) Matrigel Bio Coat (BD); Scaffold for 3-dimensional cultures AteloCell (Koken; No. CSM-50) While there are no particular limitations to the shape and the material of the culture vessel, or vessels, the use of one or more flasks, petri dishes or multi-well plates made of polystyrene is preferable.

While the components that a kit for manufacturing differentiated cell according to the present invention comprises normally include a commercially available culture medium (liquid or solid), serum (liquid or solid), a serum replacement, a growth factor, a culture medium additive (including various amino acids) and a culture vessel, there are no particular limitations to the components. For example, the culture medium may be prepared by referring to any of the compositions disclosed by different manufacturers.

A preferable embodiment of the first cell line and the second cell line of the present invention is a cell line that has both the characteristics of the first cell line and those of the second cell line. For example, the preferable embodiment may include KSC cells derived from the dorsal fin of a thread-sail filefish (*Stephanolepis cirrhifer*) as in Examples that will be described hereinafter. KSC cells are deposited in the Patent Microorganisms Depositary Center of the National Institute of Technology and Evaluation (NITE) (T 292-0818 2-5-8 Kazusa Kamatari, Kisarazu, Chiba) with the microorganism ID of "KSC", the depositary date of Jun. 1, 2012 and the accession number of "NITE BP-1369".

In still another aspect of the present invention, there is provided a cultured cell sheet made from the first cell line and/or the second cell line and obtained by culturing the first cell line and/or the second cell line of the present invention. A cultured cell sheet according to the present invention can be expected to find therapeutic applications for quality fishes, Particularly, in view of the fact that farmed fishes are poorly immune to diseases and show a high mortality rate once they are injured, a cultured cell sheet according to she present invention can take a role of reducing the morality rate of farmed fishes. Additionally, in view of the fact that artificial materials such as synthetic polymer materials and cellophane show only a limited selective permeability to different substances, a cultured cell sheet according to the present invention can be expected to find applications as living body-derived selective film that can overcome such a disadvantage. Furthermore, since individual cells of a cultured cell sheet according to the present invention produce collagen and fibronectin, it can be expected to find applications in various medical and industrial fields such as in the field of scaffolds for forming human cultured cell sheets, in the field of raw materials of capsules for transporting substances into living bodies from the viewpoint of cell-derived immunity and antibacterial effects, in the field of medical are products such as adhesive plasters and patches, in the field of testing the movements of cancer cells, in the field of immune tests and in the field of beauty packs provided as cosmetics that secrete fish-derived ingredients. Additionally, since a cultured cell sheet according to the present invention comes off from the bottom surface of the cultured cell sheet forming vessel at the time of forming the sheet, it is possible to keep on culturing the cultured cell sheet in a floating state. Thus, a cultured cell sheet according to the present invention provides an advantage that can be cultured in a floating state.

3. Method of Manufacturing a Cell Line of the Present Invention

A method of manufacturing a cell line according to the present invention is a method of manufacturing the first cell line and the second cell line of the present invention. For example, it may comprise a step of subculturing cells isolated from a living body part of a fish of the family Monacanthidae for not less than 30 times, preferably not less than 50 times, more preferably not less than 70 times (to be referred to as subculturing step hereinafter). There are no particular limitations to the subculturing step so long as it is a step of eventually obtaining a cell line according to the present invention. For example, the materials, the techniques and the conditions to be employed and the procedure of determining the produced object can be selected and executed according to the matters described, above under "1. First cell line of the present invention" and "2. Second cell line of the present invention". Additionally, one or more than one appropriate step may be arranged before, during and/or after the subculturing step comprised in the method of manufacturing a cell line according to the present invention such as a step of storing cells and returning them in the course of the subculturing step so long as the objective of manufacturing a cell line of the present invention can be achieved by additionally using such a step or steps.

4. Transformant, Method of Manufacturing the Same and Kit of the Present Invention A transformant according to the present invention is a transformant obtained by transfecting a foreign gene into a cell line of the present invention. A method of manufacturing a transformant according to the present invention comprises a step of transfecting a foreign gene into a cell line of the present invention to obtain a transformant, A method of manufacturing a foreign gene product according to the present invention comprises a step of obtaining an expression product of a foreign gene from a transformant according to the present invention.

There are no particularly limitations to the method of transfecting a foreign gene into a cell line of the present invention. Any of the existing transfection techniques that are known to those who are skilled in the art can be used to transfect a foreign gene into a cell line according to the present invention. Those techniques include lipofection techniques, electropolation techniques, microinjection techniques, calcium phosphate techniques and techniques of using baculovirus. Furthermore, to transfect a foreign gene into a cell line, the foreign gene itself may be transfected into the nucleus of a cell line of the present invention or, alternatively, a foreign gene transfecting substance such as a vector, which may typically be in the form of a recombinant vector into which the foreign gene has already been incorporated, may be employed to transfect the foreign gene into a cell line of the present invention.

There are no particular limitations to the vector to be used so long as it is an autonomously replicating vector. For example, it may be selected from commercially available vectors for mammalian cells. Specific examples of such vectors include plasmid vectors such as pcDNA3.1, Flexi HaloTag, pcDNA3.2, pcDNA4, pcDNA5, pcDNA6 and pCMV; viral vectors such as λ phage and RSV; and amphibian-derived vectors such as a vector having a xenopus-derived EF1α promoter.

There are no particular limitations to the foreign gene to be transfected into a cell line of the present invention. For example, it may be selected from genes that encode the desired protein which may be a functional protein, an edible protein, an enzyme, a protein to be used as marker, a labeling protein or the like. Since a cell line according to the present invention is a fish-derived cell line, a gene that encodes a protein that is specific to one or more than one fish may be selected as foreign gene for the purpose of the present invention. A foreign gene can be prepared according to information on the amino acid sequence of a desired protein or, alternatively, a commercially available gene may be modified to obtain a foreign gene to be transfected into a cell line of the present invention. The foreign gene may be able to encode only a type of protein or two or more than two types of protein. For instance, it the foreign gene encodes both a desired protein and an antibiotic-resistant marker, it is possible to obtain efficiently only a transformant into which a foreign gene has been transfected by utilizing the antibiotic selectivity after the gene transfection.

While there are no particular limitations to the method of producing a transformant and the method of producing a foreign gene product according to the present invention, the methods described under "6. Transfection of foreign genes into KSC cell and expression thereof" in Examples, which will be described hereinafter, may be used for the purpose of the present invention. Any of the genetic engineering techniques and the molecular biology techniques that are known to date can be employed without limitations for the purpose of executing the above methods of the present invention. For example, the methods described in Molecular Cloning: A laboratory Manual, 2nd Ed., Cold Spring Harbor Laboratory, Cold Spring Harbor, N.Y., 1989 and Current Protocols in Molecular Biology, Supplement 1-38, John Wiley & Sons (1987-1997) (the entire contents of which are incorporated herein by reference for the purpose of supporting the disclosure of the present invention) can be referred to.

It is possible to find out if a transformant is obtained by the method of manufacturing a transformant according to the present invention or not by checking as indicator the presence or absence of an expression product of the foreign gene that has been transfected into the cell line. Similarly it is possible to find out if a foreign gene product is obtained or not by the method of manufacturing a foreign gene product according to the present invention by checking as indicator the presence or absence of an expression product of the foreign gene. With the method of manufacturing a foreign gene product according to the present invention, foreign gene product may be obtained by culturing a transformant according to the present invention so as to cause foreign gene expression to take place or by culturing and proliferating a transformant according to the present invention and subsequently inducing foreign gene expression to take place. Additionally, depending on the type of the foreign gene, a foreign gene product can be obtained as expression products accumulated in a transformant according to the present invention or in the culture solution. There are no particular limitations to the method of confirming the foreign gene product so long as it is a method of detecting the presence of a specific protein that is known to those who are skilled in the art. Examples of methods that can be used to confirm the foreign gene product include Western blotting, immunoassay and chromatography, using the molecular weight of the foreign gene product and an antibody against the foreign gene product.

While there are no particular limitations to a kit for manufacturing a transformant according to the present invention so long as it comprises a cell line according to the present invention, it preferably additionally comprises a vector for transfecting a foreign gene as well as an instrument including reagents, tools and devices for transfection.

There are no particular limitations to the instrument for transfection so long as it is designed so as to be compatible with various transfection techniques. If the transfection technique to be employed is the lipofection technique, the instrument preferably includes one or more reagents such as liposome, culture media and buffer solution as well as one or more tools such as culture vessel.

5. Applications of Cell Line of the Present Invention

There are no particular limitations to applications of a cell line according to the present invention. For example, a cell line according to the present invention can find applications in the field of evaluation of physiologically active substances and in the field of screening of anti-virus agents in combination with fish viruses as well as purposive researches including cellular physiology of fishes, fish genes and their expression systems, fish viruses and experimental systems for rating environmental water pollutions, in addition to the applications that have already been described above. A cell line according to the present invention can be utilized, for example, for test substance evaluation methods comprising steps of adding a test substance into a culturing system for a cell line according to the present invention and subsequently evaluating the influence of the test substance on living cells; virus growing methods comprising steps of inoculating a virus into a culturing system for a cell line according to the present invention, and growing the virus in a nutritious culture medium suited for growing the virus; and methods of screening anti-virus therapeutic agents to be executed in combination with a virus growing method, the screening method comprising steps of adding a test substance into a culture medium where the virus is growing and subsequently evaluating the effect of the test substance on the virus. Furthermore, by applying any of the above-described methods, a cell line according to the present invention can also be utilized for methods of diagnosing viral infections, methods of manufacturing a vaccine effective for viral infections and methods of evaluating cytotoxicity. For example, cytotoxicity of a test substance can expectedly be evaluated by comparing the number of surviving cell lines of the present invention before the test substance is brought to contact with the cell lines to the number of surviving cell lines after the test substance is brought into contact with the cell lines. Additionally, methods of screening of differentiation inducing substances can expectedly be developed. Such a met may typically comprise steps of causing a cell line of the present invention to contact a test substance and steps of determining the test substance as differentiation inducing substance b detecting muscle cells, skin cells, nerve cells or adipocytes.

Hereinafter, the present invention will be described in greater detail with the use of examples, although the examples by no means limit the scope of the present invention.

Examples

1. Isolation of Cells from Thread-Sail Filefish Tissue (*Stephanolepis cirrhifer*)

A 5-mm square piece was cut off from each of the fins of a thread-sail filefish (*Stephanolepis cirrhifer*) without skinning the fish, put into a sterilized 1.5 ml tube and washed sequentially with tap water and PBS (available from Wako Pure Chemical Industries) under ice-cooled condition. Each of the washed fin pieces was subjected to replacement three times under ice-cooled condition, using 10% penicillin/streptomycin-containing PBS (available from MP Biomedicals), and thereafter left at rest for 30 minutes. The term "replacement" as used herein refers to operations of preparing a tube containing PBS by an appropriate volume, putting a fin piece into the PBS-containing tube, stirring the contents and subsequently transfecting the fin piece into another PBS-containing tube.

After leaving the fin piece at rest, the fin piece was subjected to replacement three times under ice-cooled condition, using 1% penicillin/streptomycin-containing PBS. After the treatment, trypsin EDTA (available from MP Biomedicals) in place of 1% penicillin/streptomycin-containing PBS was added onto the fin piece in the clean bench. The fin tissue piece was then cut to 1 mm square fine pieces under ice-cooled condition and left at rest at room temperature for 20 minutes. After leaving the fine fin tissue pieces at rest, they were centrifuged for several seconds. Thereafter, the supernatant was removed and the precipitated fine fin tissue pieces were treated with Leibovitz's L-15 culture medium (available from Life Technologies) several times. Thus, summarily, the fine fin tissue pieces were caused to precipitate in the tube by centrifugation and, after removing the supernatant, a fresh culture medium was added and the culture medium was agitated with the fine fin tissue pieces. Thereafter, the fine fin tissue pieces were caused to precipitate by centrifugation again and, after removing the supernatant, a fresh culture medium was added and the culture medium was agitated with the fine fin tissue pieces once again. This operation was repeated for 2 to 3 times. Table 1 shows the composition of Leibovitz's L-15 culture medium (http//ja.invitrogen.com/site/jp/ja/home/support/Product-Technical-Resources/media_formulation.80.html), (the entire contents of which are incorporated herein by reference for the purpose of supporting the disclosure of the present invention).

TABLE 1

| Ingredient | Molecular weight | Concentration (mg/L) | mM |
|---|---|---|---|
| amino acid | | | |
| glycine | 75 | 200 | 2.67 |
| L-alanine | 89 | 225 | 2.53 |
| L-arginine | 174 | 500 | 2.87 |
| L-asparagine | 132 | 250 | 1.89 |
| L-cysteine | 121 | 120 | 0.992 |
| L-glutamine | 146 | 300 | 2.05 |
| L-histidine | 155 | 250 | 1.61 |
| L-isoleucine | 131 | 250 | 1.91 |
| L-leucine | 131 | 125 | 0.954 |
| L-lysine | 146 | 75 | 0.514 |
| L-methionine | 149 | 75 | 0.503 |
| L-phenylalanine | 165 | 125 | 0.758 |
| L-serine | 105 | 200 | 1.9 |
| L-threonine | 119 | 300 | 2.52 |
| L-tryptophan | 204 | 20 | 0.098 |
| L-tyrosine | 181 | 300 | 1.66 |
| L-valine | 117 | 100 | 0.855 |
| vitamin | | | |
| chlorine chloride | 140 | 1 | 0.00714 |
| calcium D-pantotheniate | 477 | 1 | 0.0021 |
| folic acid | 441 | 1 | 0.00227 |
| niacin amide | 122 | 1 | 0.0082 |
| pyridoxine chlorate | 206 | 1 | 0.00485 |
| riboflavin 5'-sodium phosphate | 478 | 0.1 | 0.000209 |
| thiamine monophosphate | 442 | 1 | 0.00226 |
| i-inositol | 180 | 2 | 0.0111 |
| inorganic salt | | | |
| calcium chloride ($CaCl_2$) (anhydride) | 111 | 140 | 1.26 |
| magnesium chloride (anhydride) | 95 | 93.7 | 0.986 |
| magnesium sulfate ($MgSO_4$) (anhydride) | 120 | 97.67 | 0.814 |
| potassium chloride (KCl) | 75 | 400 | 5.33 |
| potassium dihydrogen phosphate ($KH_2PO_4$) | 136 | 60 | 0.441 |
| sodium chloride (NaCl) | 58 | 8000 | 137.93 |
| sodium dihydrogen phosphate ($Na_2HPO_4$) | 142 | 190 | 1.34 |
| other ingredients | | | |
| D+galactose | 180 | 900 | 5 |
| phenol red | 398 | 10 | 0.0251 |
| phenol red | 376.4 | 10 | 0.0266 |
| sodium pyruvate | 110 | 550 | 5 |

After the treatment, the fine fin tissue pieces were seeded in a 25 $cm^2$ collagen I culture flask (available from Thermo) containing Leibovitz's L-15 culture medium that contained 10% FBS (Gibco) and allowed to adhere to the bottom surface. Then, the fine fin tissue pieces were cultured there at 25° C. Each of FIGS. 1A through 1D illustrates cells migrated and developed with a central focus on each of the fine fin tissue pieces to the entire inside of the flask. Now, the subculturing procedure of the cells extracted from a dorsal fin piece will be described below.

2. Subculturing

The culture medium was removed from the inside of the culture flask and the cells adhering to the bottom surface of the flask were washed with PBS three times. Then, they were treated with TrypLE Express (Gibco) at 38° C. for 10 minutes and the cells were detached from the flask and collected. Subsequently, Leibovitz's L-15 culture medium containing 10% FBS was added to the collected cells and the cells were cultured at 25° C.

For the purpose of cell storage, after adding the culture medium to the collected cells, they were centrifuged at room temperature and at 1,100 rpm for 4 minutes and subsequently the supernatant was removed. Then, the cells were stored at −80° C., using Cell Banker 2 (available from Juji Field (BIO LAB)). Additionally, to revive the frozen cells, firstly the frozen cells were put into a half-thawed state at room temperature and the culture medium was replaced twice by Leibovitz's L-15 culture medium. For this replacement, the liquid part was taken out from the tube, where the cells were held in a half-thawed state, and transferred into a 15 ml centrifuge tube. Then, 4 ml of L-15 culture medium was added and the contents of the centrifuge tube were stirred and centrifuged. Thereafter, the supernatant was removed, and another 4 ml of L-15 culture medium was added. Then, the contents of the centrifuge tube were stirred and centrifuged again. After removing the supernatant again, Libovitz's L-15 culture medium that contained 10% FBS was added to the cells in order to be subcultured.

3. Evaluation of Cells of Established Cell Line and the Growth Rate in 25-$cm^2$ Flask The primary cultured cells that gathered along the tissue rim as shown in FIGS. 1A through 1D normally get to a cell division limit after 50 to 80 cell divisions (see Hayflick limit; Hayflick L. Moorhead POSITION, 1961, Exposure Cell Res. 25: 585-621, (the entire contents of which are incorporated herein by reference for the purpose of supporting the disclosure of the present invention). However, the doubling time of some of the cells did not deteriorate after the above number of cell divisions and kept on dividing. Such cells are defined as immortalized cells (cells of an established cell line, a cell line, etc.)

As a result of executing the above-described 1. isolation of cells from thread-sail filefish tissue and 2. subculturing, the inventors of the present invention succeeded in obtaining cells that gave rise to passages whose number was not less than 70 and experienced cell, divisions whose number was not less than 276. The inventors of the present invention named these cells as KSC cells. The KSC cells showed little change in doubling time from the first subcultured cells. Thus, the KSC cells were evaluated as cells of an established, cell line. This definition is in accordance with the definition by JRCB Cell Bank (http://cellbank.nibio.go.jp/visitercenter/whatsculture/cellculture03.html, the entire contents of which are incorporated herein by reference for the purpose of supporting the disclosure of the present invention).

It is known that the cell growth rate can vary to a large extent depending on the cell density (concentration), the culture area and other conditions for growing cells. Therefore, the inventors of the present invention compared the KSC cells with CHO cells that show a relatively high growth rate among established cell lines of mammalian cells for doubling time. The data on CHO cells are obtained from German DSMZ (http://www.dsmz.de/., the entire contents of which are incorporated herein by reference for the purpose of supporting the disclosure of the present invention), which is the second largest cell bank in the world and believed to be the most reliable cell bank and a sole cell bank in the world that store a full range of detailed cell data.

On the basis of the cell data obtained from DSMZ, it is determined by computation that, when CHO cells are seeded at a concentration of $10^6$ cells/ml in an area of about 80 cm$^2$, a state of confluence (where cells are proliferated to develop on the entire bottom surface of the flask) is reached in 76 to 96 hours and the doubling time is 24 hours. In contrast, when KSC cells are seeded at a concentration of $10^6$ cells/ml in an area of about 80 cm$^2$, a state of confluence was reached in 48 to 72 hours and the doubling time was 18.34 hours. Therefore, it was found that KSC cells have a proliferative ability similar or superior to that of CHO cell.

Besides, KSC cells were seeded at a concentration of about $0.4 \times 10^6$ cells/ml in an area of 75 cm$^2$ and cultured by using Leibovitz's L-15 culture medium containing FBS by 10% at 25° C. in the absence of $CO_2$ for 48 hours until a state of confluence was reached. Then, the total number of cells was counted by means of TC10 Automated Cell Counter (available from Bio Rad) to find that the number of cells was about $1.0 \times 10^6$ cells/ml after 24 hours of culturing and about $2.5 \times 10^6$ cells/ml after 48 hours of culturing. The doubling time was determined from the number of cells immediately after seeding the cells and the number of cells after 48 hours of culturing, using the doubling time computation software available from a web site (http://www.doubling-time.com/compute.php?lang=en), resulting in 18.16 hours. Similarly, the doubling time determined from the number of cells immediately after the cell seeding and the number of cells after 24 hours of culturing was 18.16 hours. Thus, the doubling time determined from the number of cells immediately after seeding the cells and the number of cells after 24 hours or 48 hours of culturing was 18.16 hours accorded with each other and was equal to 18.16 hours.

4. Recovery from Frozen State

Figure 2:
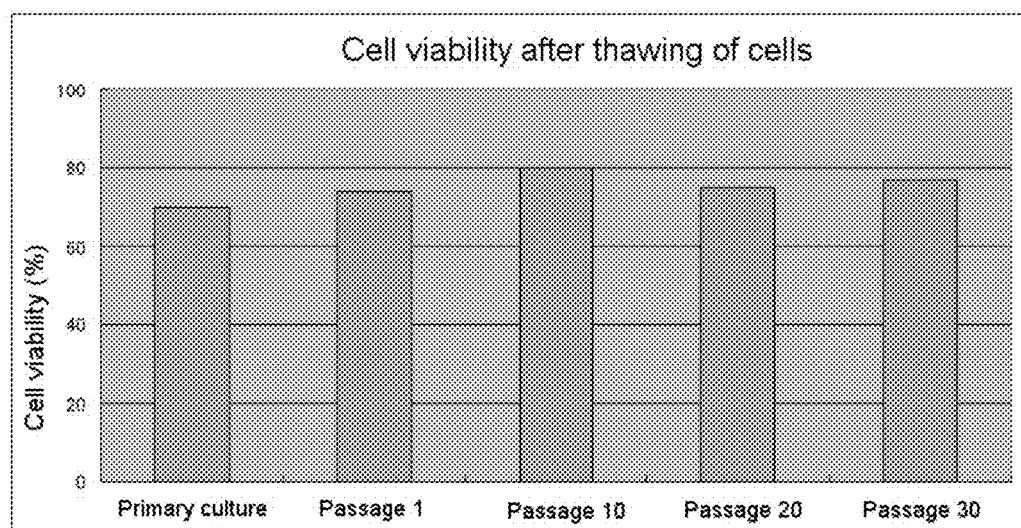
FIG. 2 is a graph illustrating the cell viabilities determined after freezing and thawing primary cells (at the time of primary culture), the first passage cells (passage 1), the 10th passage cells (passage 10), the 20th passage cells (passage 20) and the 30th passage cells (passage 30).

For the KSC cells that were cryopreserved by means of Cell Banker 2, the cell viability after thawing was assessed. FIG. 2 illustrates that the thawed KSC cells have shown a cell viability of not less than 75% regardless of the number of passages.

5. Morphological Observation of Cells

Figure 3A:
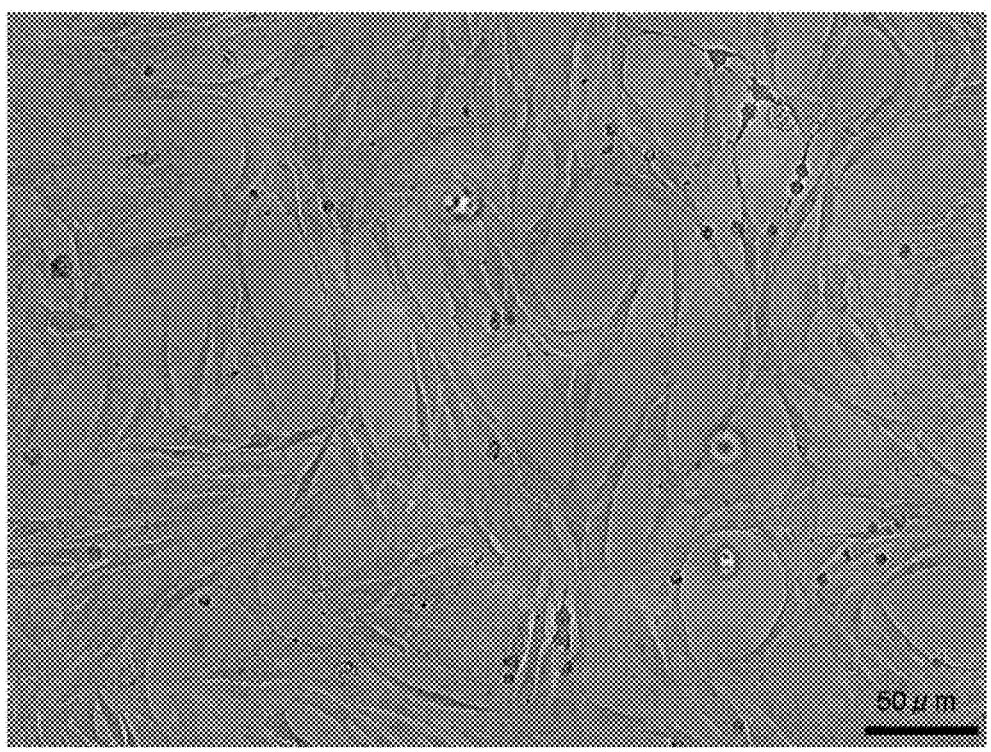
FIG. 3A is a morphological view of KSC cells as observed through an optical microscope with a magnification of ×460.
Figure 3B:
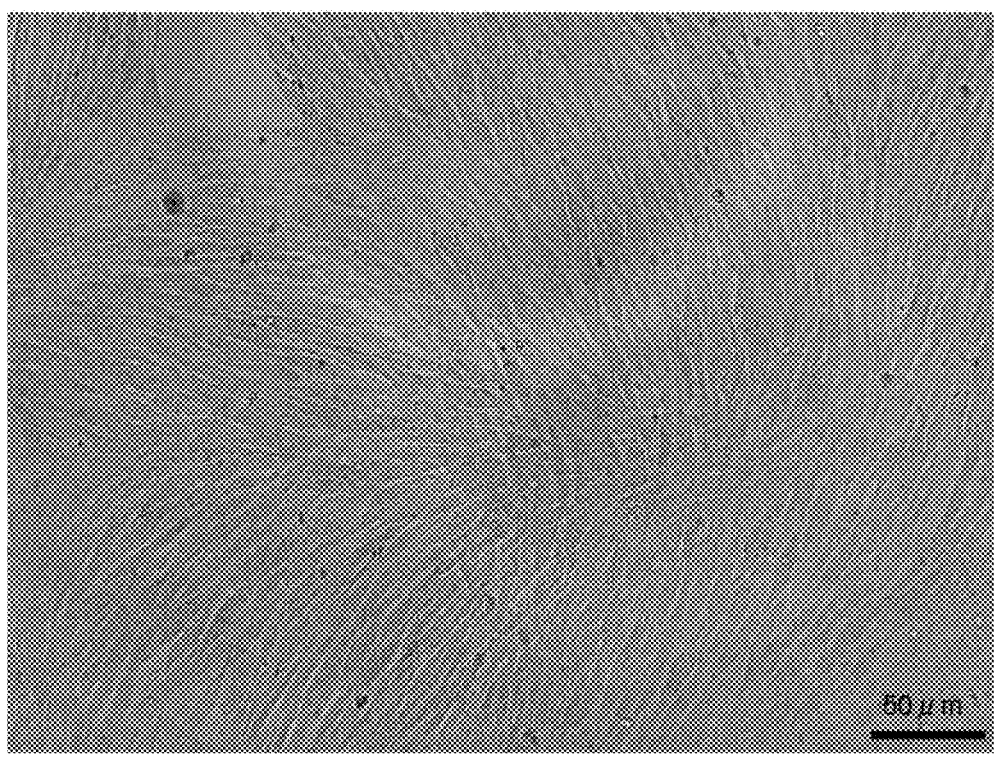
FIG. 3B is a morphological view of KSC cells that formed two layers as observed through an optical microscope with a magnification of ×460.
Figure 3C:
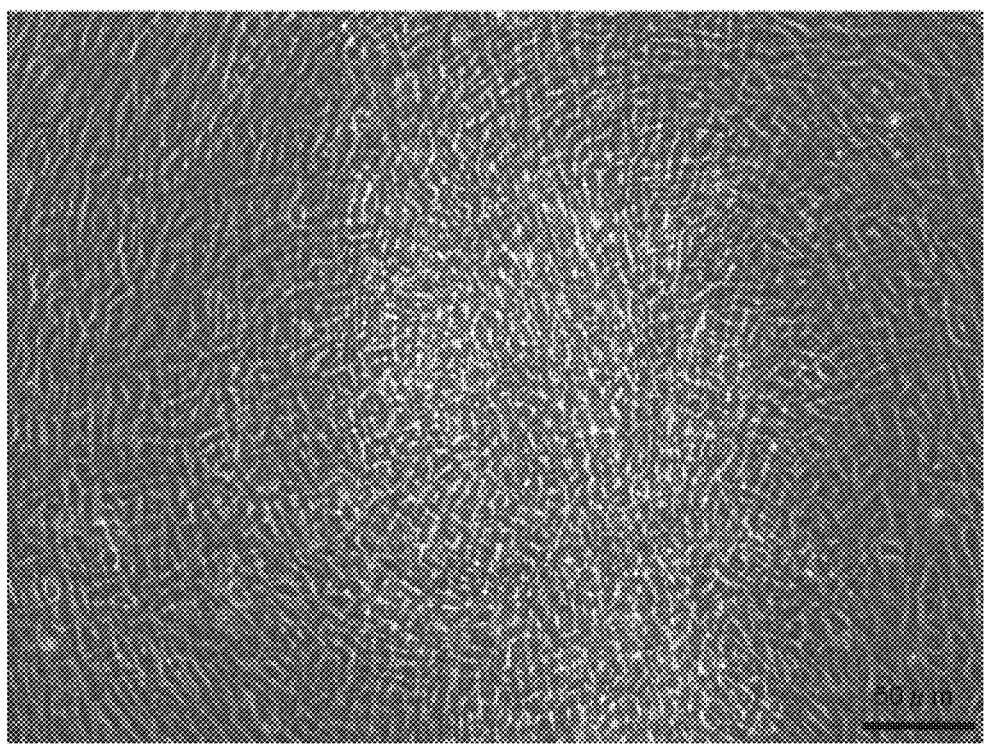
FIG. 3C is a morphological view of KSC cells that formed a multi layer as observed through an optical microscope with a magnification of ×460.

The KSC cells of the established cell line showed a morphologically fibroblast-like appearance (see FIG. 3A). Additionally, as a result of culturing KSC cells on the bottom surface of a flask, they formed a two-layered structure after getting to a state of confluence (see FIG. 3B). Furthermore, as a result of keeping on culturing KSC cells after forming the two-layered structure, they formed a multilayer structure (see FIG. 3C).

6. Transfection of Foreign Genes into KSC Cells and Gene Expression (1) Method

That various gene transfection methods that are currently being employed for mammalian cells are also applicable to KSC cells was verified by means of methods including lipofection methods including the lipofectamine method, electroporation methods, microinjection methods and methods of using baculovirus. The instructions provided by the method providers listed below were followed for details of the methods: http://tools.invitrogen.com/content/sfs/manuals/lipofectamine2000_man.pdf; http://www.invitrogten.jp/transfection/pdf/Neon quickguide_JPN.pdf; http://www.eppendorf.de/int/img/na/lit/pdf/8301-C109F-07.pdf#search=%27FemtoJetMicroinjector %27; http://probes.invitrogen.com/media/pis/mp10582.pdf#search=%27celllight%20pdf%27, (the entire contents of which are incorporated herein by reference for the purpose of supporting the disclosure of the present invention).

(2) Materials

The recombinant genes used for transfecting foreign genes include Flexi HaloTag Vector (available from Promega), Flexi HaloTag Clone (available from Promega) and pcDNA3.1 Vector (available from Life Technologies).

The following reagents etc. were employed for the transfection methods: Lipofectamine 2000 Reagent and PLUS Reagent (both available from Life Technologies), Neon Transfection System (available from Life Technologies), FemtoJet-Microinjector (available from Eppendorf) and CellLight (available from Life Technologies).

(3) Results of Gene Transfection

It was confirmed that foreign genes could be transfected into KSC cells by using the above-described techniques that are currently normally being used for mammalian cell systems.

Figure 4:
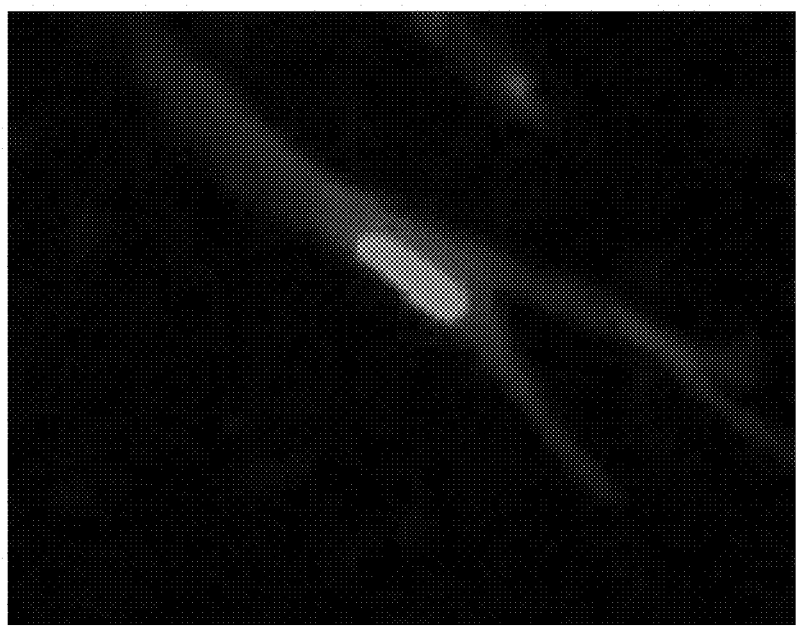
FIG. 4 is an illustration demonstrating cells expressing human-AP.
Figure 5:
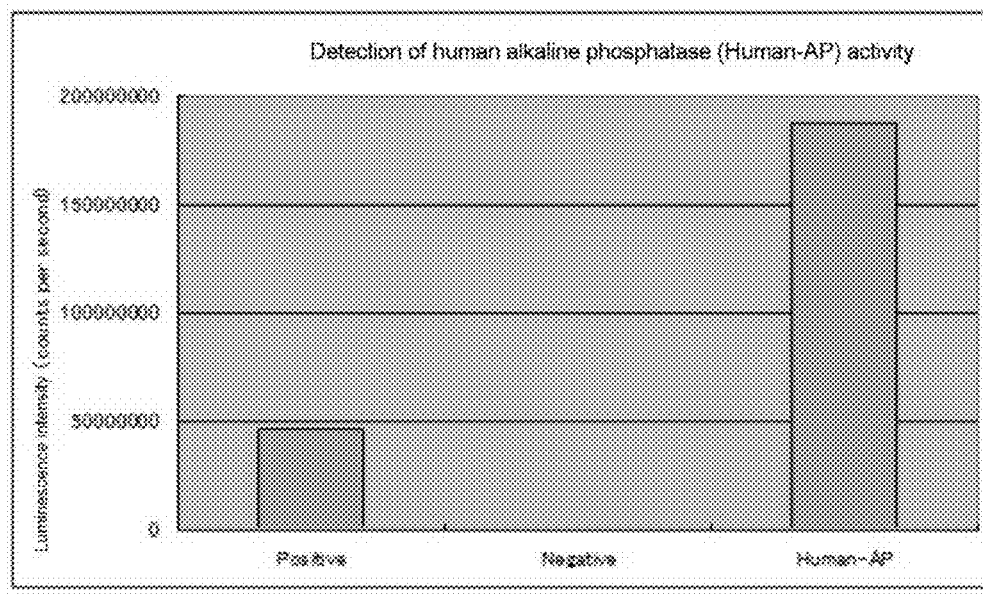
FIG. 5 is an illustration demonstrating the activity of an expression product of human-AP

(4) Expression of Human Alkaline Phosphatase (Human AP) that is a Foreign Gene Product The expression of Flexi HaloTag human-AP that is a gene product of foreign genes transfected into KSC cells was fluorescence-detected by means of HaloTag Oregon Green Ligand (see FIG. 4). The activity of the produced human AP was measured by means of Ziva Ultra SEAP Plus Detection Kit (available from Funakoshi) (see FIG. 5). As seen from FIGS. 4 and 5, the expressions of the foreign genes transfected into KSC cells were confirmed and, furthermore, the expression products were active.

(5) Expression of Foreign Gene Product Human Paraoxonase (PON)

Figure 6:
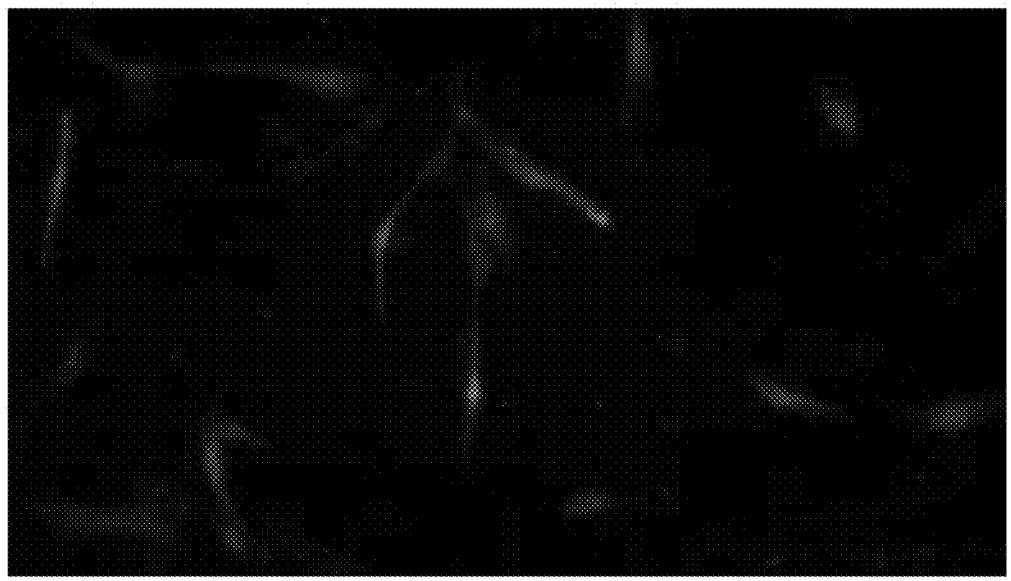
FIG. 6 is an illustration demonstrating an expression by fusion proteins of PON and Halotag.

The expression of Flexi HaloTag PON, which is a gene product of a foreign gene transfected into KSC cells, was fluorescence-detected by means of TMR-Ligand (see FIG. 6). As seen from FIG. 6, the expression of the foreign gene transferred into KSC cells was confirmed.

(6) Expressions of Foreign Gene Product Fluorescent Proteins

Figure 7A:
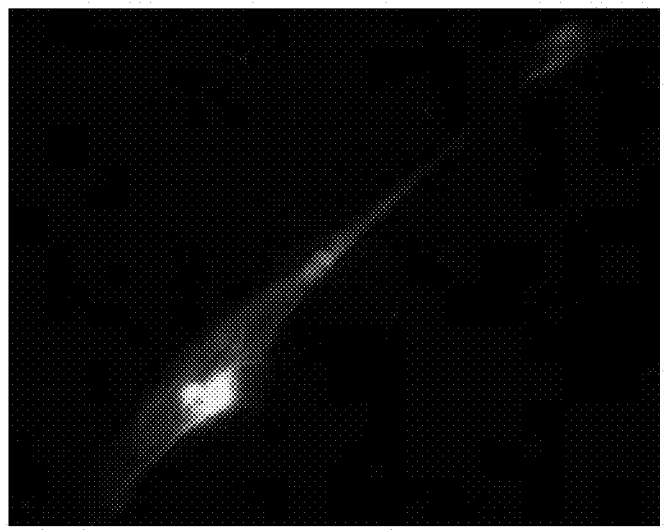
FIG. 7A is a view obtained by observing cells expressing cyan-fluorescent-protein, yellow-fluorescent-protein and calmodulin, which are fluorescent fusion proteins.
Figure 7B:
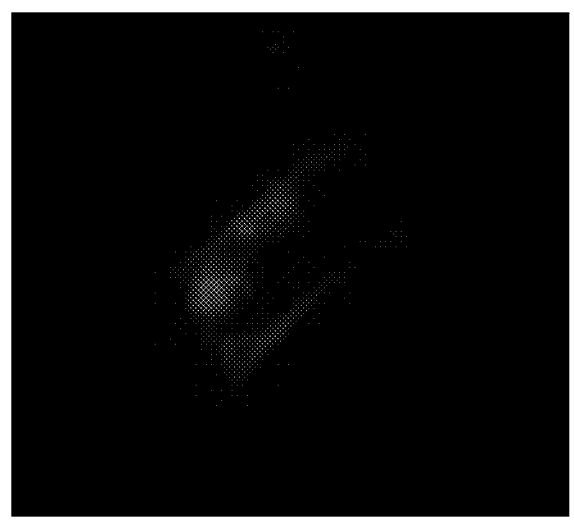
FIG. 7B is a view obtained by observing cells expressing red-fluorescent protein and G glycoprotein of vesicular stomatitis virus, which are fluorescent fusion proteins.
Figure 7C:
FIG. 7C is a view obtained by observing cells expressing green fluorescent protein, which is a fluorescent protein.

Cells that expressed cyan fluorescent protein-yellow florescent protein and calmodulin; red florescent protein and G glycoprotein of vesicular stomatitis virus; and green fluorescent protein which are gene products of the foreign genes transferred into KSC cells and fluorescent proteins were observed through a fluorescence microscope (see FIGS. 7A through 7C). As seen from FIGS. 7A through 7C, the expressions of the foreign genes transferred into KSC cells were confirmed.

7. Evaluation of Cell Stability at Transfection (Gene Transfection)

Figure 8:
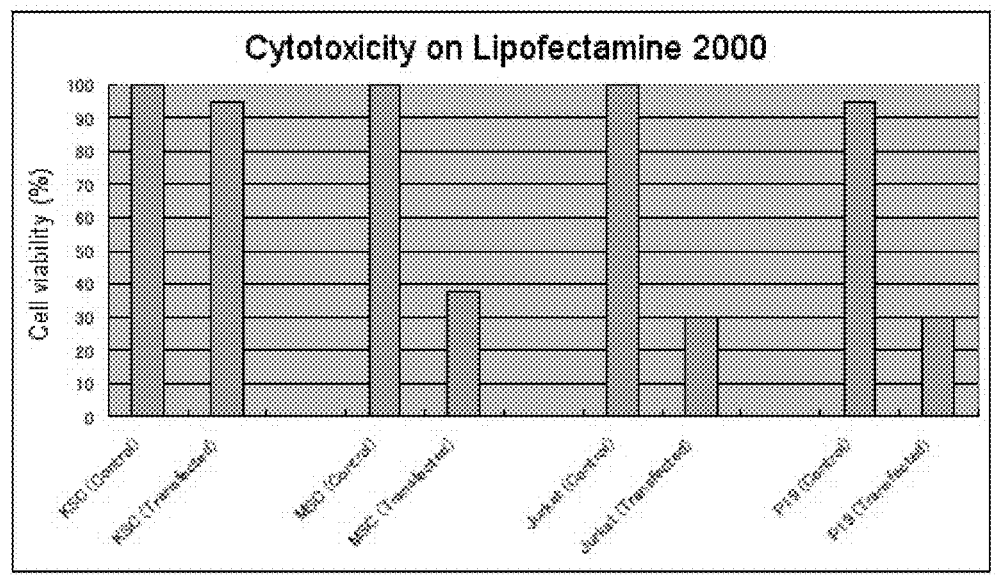
FIG. 8 is a graph verifying the cytotoxicity of each cell after gene induction with the use of Lipofectamine method.
Figure 9A:
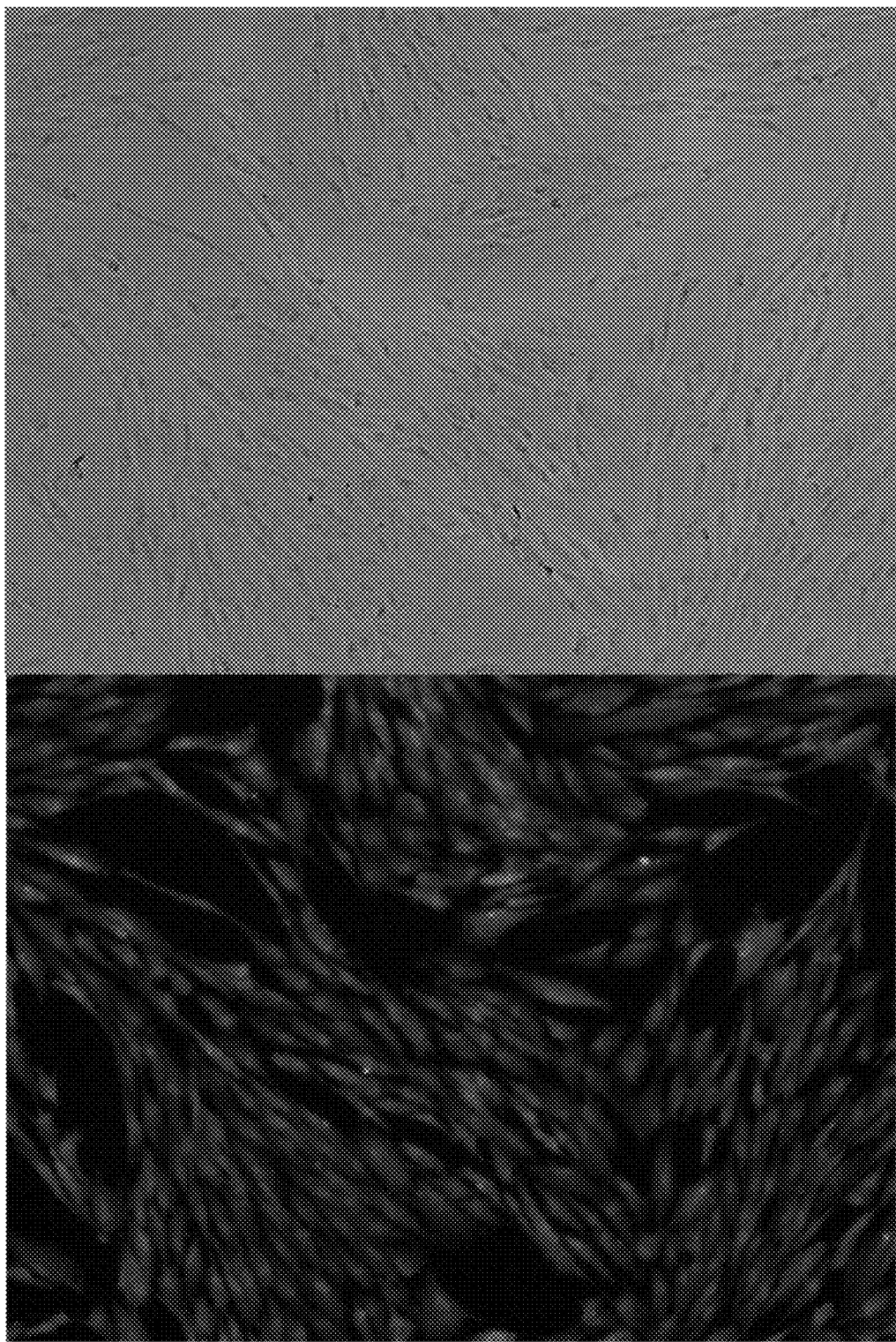
FIG. 9A is an illustration demonstrating that KSC cells are cells positive for TRA-1-60, which is a cell marker specific to pluripotent stem cells. The upper half shows the result of an observation through an optical microscope and the lower half shows the result of an observation through a fluorescence microscope.
Figure 9B:
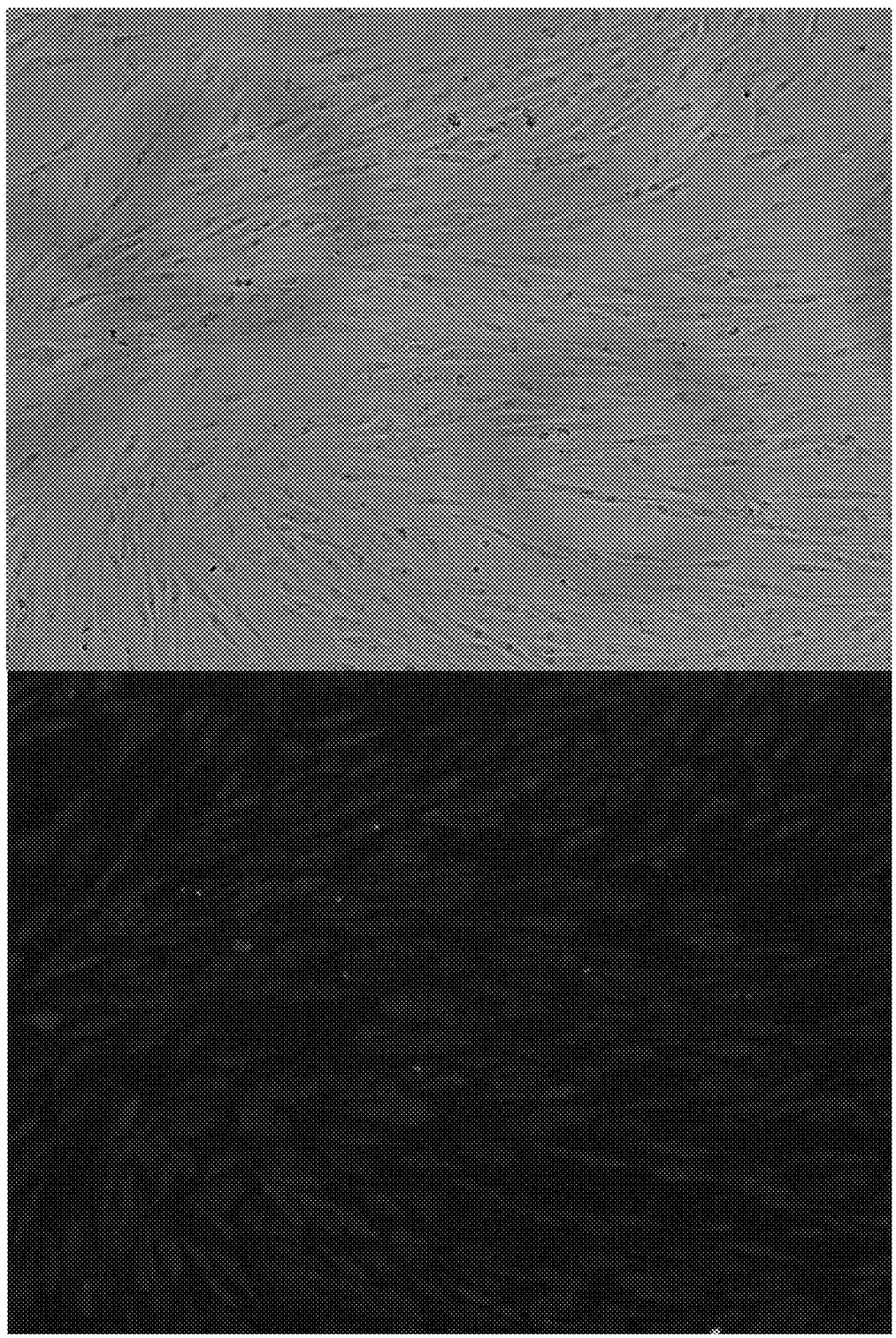
FIG. 9B is an illustration demonstrating that KSC cells are cells positive for OCT4, which is a cell marker specific to pluripotent stem cells. The upper half shows the result of an observation through an optical microscope and the lower half shows the result of an observation through a fluorescence microscope.
Figure 9C:
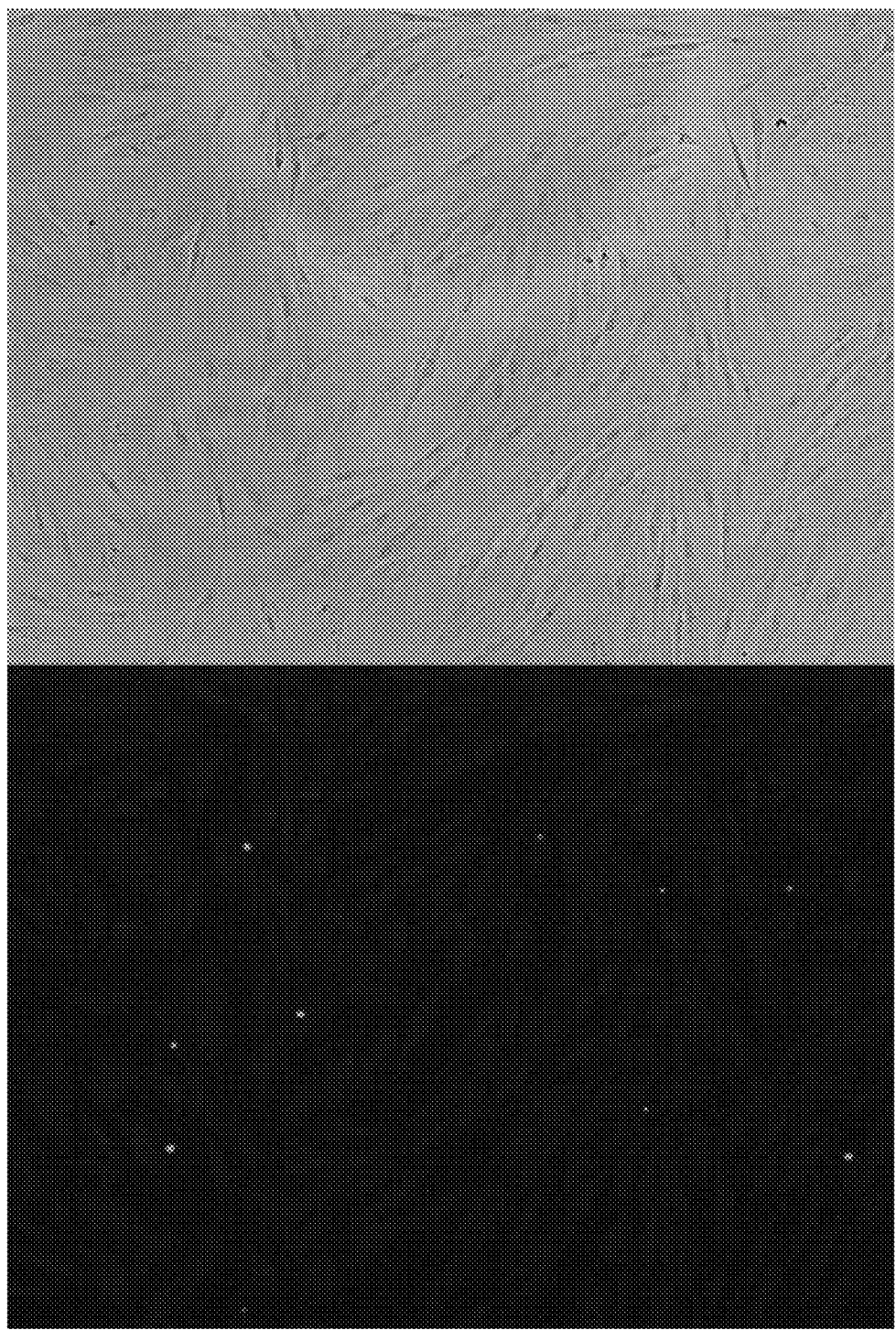
FIG. 9C is an illustration demonstrating that KSC cells are cells positive for SSEA-3, which is a cell marker specific to pluripotent stem cells. The upper half shows the result of an observation through an optical microscope and the lower half shows the result of an observation through a fluorescence microscope.

The cytotoxicity (resistivity) at a gene transfection by the above Lipofectamine method was compared and verified by using KSC cells, rat mesenchymal stem cells (MSC), human acute T-cell leukemia cell lines (Jurkat) and mouse embryonal carcinoma cells (P19). As a result, the viability of KSC cells was found to be not less than 90% after the gene transfection (already transfected) on the basis of comparison with the control (before a gene transfection) and hence show an excellent cell stability if compared with other cells (FIG. 8).

8. Verification of Possibility of High Density Culturing of KSC Cells

The possibility of suspension culturing of KSC cells was verified. It was confirmed that KSC cells proliferated when they were cultured by using a spinner flask and Leibovitz's L-15 culture medium containing FBS by 10% at 25° C. in the absence of $CO_2$ and at a spinning rate of 100 rpm. It was also confirmed that, when suspension-cultured in the above conditions, KSC cells divide themselves at a rate of once in every about 26 hours as a result of counting the number of cells by means of TC10 Automated Cell Counter (available from Bio Rad).

9. Verification of Possibility of Serum-Free Culturing

The doubling time of KSC cells under serum-free culturing was examined by way of culturing (serum-free culturing) using a 25-$cm^2$ collagen I-coated cell culture flask and Leibovitz's L-15 culture medium and, for the purpose of comparison, also by way of culturing (serum replacement culturing) using a 25-$cm^2$ collagen I-coated cell culture flask, Leibovitz's L-15 culture medium and a serum replacement additive (KSR; available from Life Technologies). As a result, it was found that, if compared with ordinary culturing with the addition of FBS serum, serum-free culturing could allow KSC cells to proliferate although the doubling time of KSC cells was prolonged. Additionally, it was found that KSC cells can be cultured with a growth rate that is substantially same as the growth rate of ordinary culturing when a serum replacement additive is used.

10. Chromosome Analysis (1) Reagents

A KaryoMAX-COLCEMID-PBS Solution (10 μg/ml) (available from Life Technologies) was used as colcemid solution and a 0.075M KCl solution was used as low hypotonic solution. A methanol:acetic acid=3:1 solution was prepared as fixative solution at the time of use and actually put to use.

(2) Preparations of Chromosome Samples

Because colcemid stops the cell cycle at the M Phase, the number of cells in the M phase increases as a result of a colcemid treatment. However, with a prolonged treatment time, the chromosome is shortened to make it impossible to analyze the chromosome. Therefore, among the cells that reached to a state of confluence by about 80 to 90%, the cells in the logarithmic growth phase were selected and a colcemid solution was added to them to realize a concentration of 0.02 μg/ml. Subsequently they were incubated continuously for about 5 hours and a colcemid treatment was executed on them.

Thereafter, the treated cells were tripsinized and detached. Subsequently, a cell detachment solution was put into a 15 ml tube and the contents of the tube were centrifuged at a rate of 1,100 rpm for four minutes. Then, the supernatant was removed and the cells were collected. Since the cells influence the colcemid treatment time, the operation was carried out quickly.

Then, a small amount of a hypotonic solution was added by means of a pipet to the 15 ml tube that contained the collected cells and the collected cells were dispersed by gentle pipetting. Then, a hypotonic solution was added into the tube that contained the dispersed cells until the final volume got to 1.5 ml and subsequently the cells were dispersed again by pipetting. The cells dispersed in the hypotonic solution were left at rest at room temperature for 20 minutes so as to be subjected to a hypotonic treatment.

Thereafter, a fixative solution was added slowly to make the total volume to be equal to about 10 ml and gently stirred to immobilize the cells. Furthermore, the contents of the tube were centrifuged at a rate of 1,100 rpm for 4 minutes and the supernatant was removed. Then, a few drops of a new fixative solution was added to the cells that had been precipitated, and the cells were dispersed by pipetting. Furthermore, after further adding a fixative solution by about 10 ml, the entire contents of the tube was stirred. The above operation was repeated twice to completely immobilize the cells. The immobilized cells were stained with Quinacrine-Hoechst (available from Wako Pure Chemical Industries) and then observed through an optical microscope.

As a result of the observation, it was found that the cell population of KSC cells included three types of cell lines that contained 32 chromosomes, 33 chromosomes and 66 chromosomes respectively. Of normal thread-sail filefishes (*Stephanolepis cirrhifer*), female fishes have 33 chromosomes and male fishes have 34 chromosomes. Of the cell population of KSC cells, 90% had 33 chromosomes just like female thread-sail filefishes (*Stephanolepis cirrhifer*). However, the remaining 10% of the cell population had 32 chromosomes or 66 chromosomes.

11. Multipotency Analysis by Means of Stem Cell Markers (1) Method

KSC cells were immunochemically stained by following the procedures shown below. In addition, a PBS solution containing 10% FBS and 0.1% Triton X-100 was employed as blocking buffer. A PBS solution containing 3% goat serum and 0.1% Triton X-100 was employed as antibody dilution buffer.

Firstly, after culturing KSC cells in a culturing flask until they got to a state of confluence, the culture medium was removed and the KSC cells were washed with PBS twice at room temperature. Four percent of paraformaldehyde was added to the cells and left at rest for 20 minutes at room temperature to immobilize the cells. Then, the paraformaldehyde was removed and the immobilized cells were washed with PBS three times at intervals of 10 minutes. The blocking buffer was added and the cells in the flask were left at rest for 1 hour at room temperature. Thereafter, the blocking buffer was removed and the blocking-treated cells were washed with PBS once. Then, the primary antibody that had been diluted to 100 folds by an antibody dilution buffer (ES/iPS Cell Characterization Kit; available from Funakoshi) was added to cause a primary antibody reaction to take place on the cells overnight at 4° C. The next day, after removing the primary antibody, the reacted cells were washed with PBS five times at regular intervals of 10 minutes. Thereafter, a secondary antibody that had been diluted in the antibody dilution buffer was added to the cells and the cells were left at rest for 1 hour at room temperature to cause a secondary antibody reaction to take place on the cells. As for secondary antibodies, Anti-IgG+IgM (H+L), Mouse, Goat-Poly, FITC was used against anti-TRA-1-60 antibody and Anti-RAT IgM (mu chain) (GOAT), DyLight 488 was used against anti-SSEA-3 antibody, while Anti-IgG (H+L), Rabbit, Goat-Poly, DyLight 488 was used against anti-NANOG antibody; and Anti-IgG (H+L), Rabbit, Goat-Poly, DyLight 488 was used against anti-OCT4 antibody. At this time, the plate on which the cells were immobilized was protected against light. Thereafter, the secondary antibodies were removed and, after the reaction, the cells were washed with PBS four times at regular intervals of 10 minutes. At this time again, the plate was protected against light. The washed cells were observed by means of FLoid Cell Imaging Station (available from Life Technologies).

(2) Results

FIGS. 9A through 9D show the results of observation. Most of the KSC cells were positive in terms of expressing TRA-1-60, OCT4 and SSEA-3. The expression intensity was in the descending order of TRA-1-60, OCT4 and SSEA-3. In contrast, the KSC cells were negative in terms of expressing NANOG and, if positive, they were only slightly expressing NANOG.

Shohei Wakao et al., PNAS, Jun. 14, 2011, Vol. 108, No. 24. pp. 9875-9880, (the entire contents of which are incorporated herein by reference for the purpose of supporting the disclosure of the present invention) reports the existence of human dermal fibroblasts (Muse cells) having multipotency. From the above results, it may be safe to presume that KSC cells may be cell lines having multipotency on the basis that they are fibroblast-like cells that express cell markers specific to multipotent stem cells such as TRA-1-60, OCT4 and SSEA-3.

12. Differentiation Induction Experiments

Since it is presumable that KSC cells can be cell lines having multipotency, the inventors of the present invention tried to cause KSC cells to differentiate into various cells by using various culture media and culturing conditions. The morphological appearances of the obtained cells were observed through optical microscopes with a magnification of 460.

(1) Morphology of KSC Cells (Prior to Induced Differentiation)

KSC cells were cultured in a collagen-coated flask by using Leibovitz's L-15 culture medium that contained FBS by 10% (v/v). FIG. 10A shows the result of observation of the cells after the culturing. The fibroblast-like morphological appearances of the cells as shown in FIG. 10A can be presumed as those of KSC cells before they differentiated into other cells.

(2) Differentiation into Muscle Cell-Like Cells

KSC cells with an initial cell density of 1 to $4 \times 10^5$ cells/ml were cultured in a 25-cm$^2$ or 75-cm$^2$ collagen-coated flask by using AIM V culture medium (available from Life Technologies; No. 087-0112DK) containing FBS by 10% (v/v) in the absence of $CO_2$ at 25° C. until they got to a state of 90% or more confluence. After the culturing, the cells appeared morphologically like muscle cells (see FIG. 10B). Additionally, after the culturing, the cells were found to be cells having proliferation potency.

(3) Differentiation into Epithelial Cell-Like Cells

KSC cells with an initial cell density of 1 to $4 \times 10^5$ cells/ml were cultured in a 25-cm$^2$ or 75-cm$^2$ uncoated flask by using Leibovitz's L-15 culture medium containing FBS by 10% (v/v) in the absence of $CO_2$ at 25° C. until they got to a state of 90% or more confluence. After the culturing, the cells appeared morphologically like epithelial cell (see FIG. 10C). Additionally, after the culturing, the cells were found to be cells that were capable of proliferation.

(4) Differentiation into Nerve Cell-Like Cells

KSC cells with an initial cell density of 1 to $4 \times 10^5$ cells/ml were cultured in a 25-cm$^2$ or 75-cm$^2$ uncoated flask by using serum-free Leibovitz's L-15 culture medium containing FBS by 10% (v/v) in the absence of $CO_2$ at 25° C. until they got to a 90% or more confluent state. After the culturing, the cells appeared to form cell-like fused bodies having nerve-like axons (see FIG. 10D). Additionally, after the culturing, the cells were not capable of proliferation but had extensibility. Furthermore, after the culturing, the cells were positive for cell markers that were specific to nerve cells.

KSC cells were cultured in a similar manner by using various combinations of culture vessels, serums and culture media to induce differentiation. As a result, adipocyte-like cells, fibrocyte-like cells, hepatocyte-like cells, immune cell-like cells appearing like branches of a rose tree and huge cocoon-like fused cells were obtained (see FIGS. 10E through 10I). In particular, the fused cells shown in FIG. 10I were positive for alkaline phosphatase activity (see FIG. 11A) and also positive for NANOG (see FIG. 11B). Additionally, the fused cells were also positive for TRA-1-60, OCT4 and SSEA-3 (see FIGS. 11C through 11E).

13. Preparation of Cultured Cell Sheets

Figure 12:
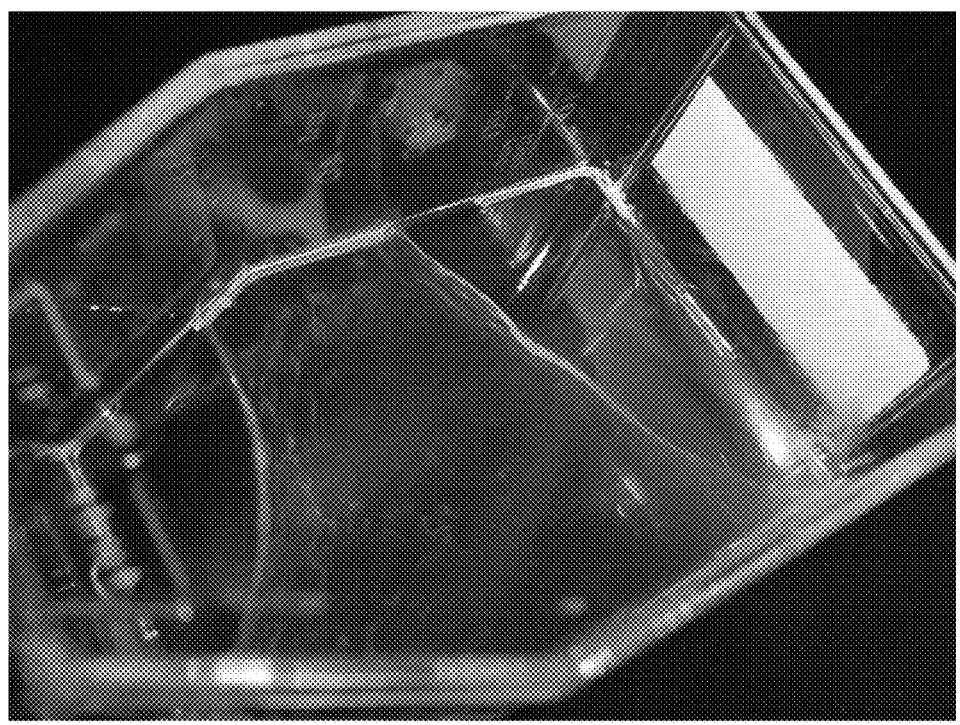
FIG. 12 is an illustration demonstrating a cell sheet obtained by culturing KSC cells.

KSC cells ($1 \times 10^5$ cells/ml) were seeded in a collagen I-coated flask by using Leibovitz's L-15 culture containing FBS by 10%. The culture medium was replaced repeatedly once in every three days and the culturing was continued 1 to 3 months to find that a thin film-like cultured cell sheet was formed (see FIG. 12). Besides, differentiation inducer Noggin (available from Human Zyme) or G-CSF (also available from Human Zyme) was added to the culture medium as growth factor-culture medium additive so as to realize a final concentration of 500 pg/ml to make it possible to enhance the sheet forming efficiency and boost the cultured cell sheet forming rate. The formed cultured cell sheet was a sheet-shaped or thin-film-shaped product in which the cells were bound to each other and which was characterized in that it had an appearance of a fine texture and that the cells in the sheet were visually not recognizable in morphology.

Acceptance Number

*Stephanolepis cirrhifer* KSC NITE BP-1369.

The invention claimed is:

1. A cell line or a passage strain thereof derived from a dorsal fin of a thread-sail filefish (*Stephanolepis cirrhifer*), wherein the cell line or the passage strain thereof has the following properties (1) to (4):
    (1) a property of being capable of being subcultured substantially without limitations so that the cell line or a passage strain can undergo cell divisions for not less than 100 times;
    (2) a property of showing a doubling time of about 14 to 24 hours when the cell line or the passage strain thereof is cultured in a culture vessel having a bottom area of 75 cm$^2$, using a Leibovitz's L-15 culture medium containing FBS by 10%, at 25° C. in the absence of $CO_2$ with an initial cell number of about $1.0 \times 10^6$ cells/ml;
    (3) a property of being positive for each of the cell markers TRA-1-60, OCT4 and SSEA-3; and
    (4) a property of having a number of chromosomes that is in accordance with the frequency distribution having a maximum value of 66, a minimum value of 32 and a mode of 33.

2. The cell line or the passage strain thereof according to claim 1, wherein the cell line or the passage strain thereof further has the following property (5):
    (5) a property of being similar to fibroblast in morphology.

3. The cell line or the passage strain thereof according to claim 1 or 2, wherein the cell line or the passage strain thereof further has the following property (6):
    (6) a property of being able to be cultured to form a multilayer structure.

4. The cell line or the passage strain thereof according to claim 1, wherein in the property (4), the frequency of 33 chromosomes of the mode takes about 90% of all the frequencies in the frequency distribution.

5. The cell line or the passage strain thereof according to claim 1 or 2, wherein the cell line or the passage strain thereof further has an ability of differentiating into at least a type of cell selected from a group consisting of muscle cells, muscle cell-like cells, epithelial cells, epithelial cell-like cells, nerve cells, nerve cell-like cells, adipocytes, adipocyte-like cells, immune cells, immune cell-like cells, hepatocytes and hepatocyte-like cells.

6. A cell line or a passage strain thereof derived from the dorsal fin of a thread-sail filefish (*Stephanolepis cirrhifer*) with the accession number of NITE BP-1369.

7. A method of manufacturing the cell line or the passage strain thereof according to claim 1, comprising a step of subjecting a cell isolated from a dorsal fin of a thread-sail filefish (*Stephanolepis cirrhifer*) to subcultures for not less than 70 times.

8. A transformant obtained by transfecting a foreign gene into the cell line or the passage strain thereof according to claim 1.

9. A method of manufacturing a transformant, comprising a step of transfecting a foreign gene into the cell line or the passage strain thereof according to claim 1 to obtain a transformant.

10. A method of manufacturing an expression product of a foreign gene comprising a step of obtaining an expression product of a foreign gene from a transformant obtained by transfecting the foreign gene into the cell line or the passage strain thereof according to claim 1.

11. A kit for manufacturing a transformant, comprising the cell line or the passage strain thereof according to claim 1, a vector and an instrument for transfection.

12. A kit for manufacturing a differentiated cell, comprising the cell line or the passage strain thereof according to claim 1, a culture medium and a culture vessel.

13. The kit according to claim 12, wherein the kit further comprises serum.

14. The kit according to claim 13, wherein the serum is a type of serum selected from a group consisting of mammalian serum, fish serum and a serum replacement.

15. The kit according to claim 12, wherein the culture medium is at least a type of culture medium selected from a group consisting of culture media for mammalian cells, culture media for insect cells and culture media for fish cells.

16. The kit according to claim 12, wherein the culture vessel is at least a type of culture vessel selected from a group consisting of culture vessels coated at the bottom surface with cell adhesion molecules and culture vessels not coated at the bottom surface with any cell adhesion molecules.

17. A method of manufacturing a muscle-like cell, comprising a step of culturing the cell line or the passage strain thereof according to claim 1 in a culture vessel coated at the bottom surface with collagen, using a AIM V culture medium containing 10% v/v mammalian serum, fish serum or a serum replacement, in the absence of $CO_2$ at 25° C.

18. A cultured cell sheet comprised of the cell line or the passage strain thereof according to claim 1.

19. A method of manufacturing an epithelial-like cell, comprising a step of culturing the cell line or the passage strain thereof according to claim 1 in a culture vessel not coated at the bottom surface with any cell adhesion molecules, using Leibowitz's L-15 culture medium containing 10% v/v mammalian serum, fish serum or a serum replacement, in the absence of $CO_2$ at 25° C.

\* \* \* \* \*